(12) United States Patent
Bosslet et al.

(10) Patent No.: US 7,605,136 B2
(45) Date of Patent: Oct. 20, 2009

(54) EFFECTOR CONJUGATES, METHODS FOR THEIR PREPARATION AND THEIR PHARMACEUTICAL USE

(75) Inventors: Klaus Bosslet, Berlin (DE); Holger Hess-Stumpp, Berlin (DE); Jens Hoffmann, Muhlenbeck (DE); Ulrich Klar, Berlin (DE); Andrea Rotgeri, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 224 days.

(21) Appl. No.: 10/728,098

(22) Filed: Dec. 5, 2003

(65) Prior Publication Data
US 2004/0167083 A1    Aug. 26, 2004

Related U.S. Application Data
(60) Provisional application No. 60/431,197, filed on Dec. 6, 2002.

(30) Foreign Application Priority Data
Dec. 5, 2002    (DE) ................. 102 56 982

(51) Int. Cl.
*A61K 31/70*    (2006.01)
*C07H 17/00*    (2006.01)

(52) U.S. Cl. ............ 514/35; 514/25; 536/4.1; 536/17.1; 536/17.4

(58) Field of Classification Search ........ 536/4.1, 536/7.1, 17.4; 514/25, 35
See application file for complete search history.

(56) References Cited

U.S. PATENT DOCUMENTS

| | | | |
|---|---|---|---|
| 5,621,002 A | 4/1997 | Bosslet et al. | |
| 5,877,158 A | 3/1999 | Bosslet et al. | |
| 5,955,100 A | 9/1999 | Bosslet et al. | |
| 6,146,658 A | 11/2000 | Bosslet et al. | |
| 6,387,927 B1 * | 5/2002 | Altmann et al. | 514/311 |
| 6,441,186 B1 * | 8/2002 | Nicolaou et al. | 548/204 |

FOREIGN PATENT DOCUMENTS

| | | |
|---|---|---|
| EP | 0 595 133 A2 | 5/1994 |
| EP | 0 647 450 A1 | 4/1995 |
| EP | 0 648 503 A1 | 4/1995 |
| WO | WO 2004/012735 A2 | 2/2004 |

OTHER PUBLICATIONS

International Search Report dated May 17, 2004.
Bosslet, K. et al., "Elucidation of the Mechanism Enabling Tumor Selective Prodrug Monotherapy" Cancer Research, Amer. Assoc. for Cancer Res., (1998) pp. 1195-1201, XP002108804.
Database Crossfire Beilstein, Online, Beilstein Institut zur Förderung der Chemischen Wissenschaften, Frankfurt, Main, DE, XP002278521.
Database Crossfire Beilstein, Online, Beilstein Institut zur Förderung der Chemischen Wissenschaften, Frankfurt, Main, DE, XP002278522.
Database Crossfire Beilstein, Online, Beilstein Institut zur Förderung der Chemischen Wissenschaften, Frankfurt, Main, DE, XP002278523.
Nicolaou K. et al., "Chemical Biology of Epothilones", Angewandte Chemie, International Edition, Verlag Chemie, Weinheim, DE, vol. 37, No. 15 (1998), pp. 2014-2045.
Beilstein Registry No. 8101198.
Beilstein Registry No. 8101202.
Beilstein Registry No. 9104283.
Beilstein Registry No. 8101197.
Beilstein Registry No. 8665382.
Beilstein Registry No. 9103332.

* cited by examiner

*Primary Examiner*—Elli Peselev

(57) ABSTRACT

Conjugates of epothilones and epothilone derivatives (as effectors) with suitable saccharides or saccharide derivatives (as recognition units) are described. Their production is carried out by the recognition units being reacted with suitable linkers, and the compounds that are produced are conjugated to the effectors. The pharmaceutical use of the conjugates for treating proliferative or angiogenesis-associated processes is described.

21 Claims, No Drawings

EFFECTOR CONJUGATES, METHODS FOR THEIR PREPARATION AND THEIR PHARMACEUTICAL USE

This application claims the benefit of the filing date of U.S. Provisional Application Ser. No. 60/431,197 filed Dec. 6, 2002.

In recent decades, a series of highly effective new chemotherapy agents for the therapy of tumors was developed. Despite all of these efforts, the treatment options and the therapeutic window are limited by the high intrinsic toxicity of these pharmaceutical agents.

Only a small portion of the amount of substance administered reaches the tumor (Anderson et al., Clin Pharmacokinet 27, 191-201, 1994; Thorpe et al., Breast Canc Res Treat 36, 237-251, 1995), while the maximum amount of substance is taken up by healthy tissue and thus is responsible for many of the undesirable side effects.

For this reason, the selective release of systemically administered chemotherapy agents at the target site always represents a scientific challenge. More recent developments aim at, for example, detoxifying cytostatic agents by conversion into a prodrug form and cleaving the non-toxic prodrug only when reaching the tumor by tumor-associated enzymes. A validation of this concept could be achieved by Bosslet (Bosslet et al., Canc Res 58, 1195-1201, 1998) in the example of a non-toxic prodrug, based on doxorubicin, which was chemically linked to glucuronic acid. In this case, the finding that an elevated lysosomal β-D-glucuronidase activity is observed in the necrotic areas of many tumors was used.

On the one hand, the relatively low cytotoxicity of the chemotherapy agent doxorubicin that was used and that required a high dosage of the prodrug proved disadvantageous, and on the other hand, the relatively quick development of resistance against doxorubicin itself proved disadvantageous.

The new structural class of the epothilones and analogs thereof primarily offers a possibility of avoiding these drawbacks. Most natural or synthetically modified compounds from their structural class exert their full antiproliferative activity against the most varied tumor cells that are resistant to other chemotherapy agents. The active strength relative to these cells can be up to 10,000× greater, compared to chemotherapy agents that are used in clinical practice, such as, for example, taxol, doxorubicin, cis-platinum or camptothecin.

Within the scope of this invention, surprisingly enough, a possibility has now been found to link the chemically very sensitive highly-functionalized active ingredient class of the epothilones and analogs thereof with a recognition unit that contains a saccharide or a saccharide derivative via different linkers to various positions of the active ingredient.

The object of this invention is thus based on, i.a.,
1. Finding a method to link highly active active ingredients from the structural class of the epothilones and epothilone derivatives with suitable recognition units via linkers, whereby the resulting conjugates are adequately stable both chemically and metabolically for a development of pharmaceutical agents and are superior to the underlying epothilones or epothilone derivatives with respect to their therapeutic range, their selectivity of action and/or undesirable toxic side effects and/or their active strength;
2. Synthesizing suitable linker-recognition units;
3. Developing a method to link these linker-recognition units with epothilones to conjugates.

This invention correspondingly comprises conjugates of general formula I

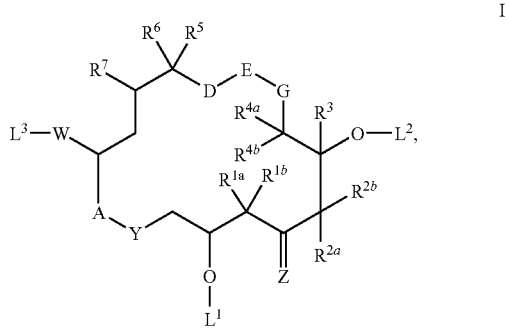

in which
$R^{1a}$, $R^{1b}$, independently of one another, are hydrogen, $C_1$-$C_{10}$ alkyl, aryl, aralkyl, or together a —$(CH_2)_m$— group, in which m is 2 to 5, $R^{2a}$, $R^{2b}$, independently of one another, are hydrogen, $C_1$-$C_{10}$ alkyl, aryl, aralkyl, or together a —$(CH_2)_n$— group, in which n is 2 to 5, or $C_2$-$C_{10}$ alkenyl, or $C_2$-$C_{10}$ alkinyl, $R^3$ is hydrogen, $C_1$-$C_{10}$ alkyl, aryl or aralkyl, and $R^{4a}$, $R^{4b}$, independently of one another, are hydrogen, $C_1$-$C_{10}$ alkyl, aryl, aralkyl, or together a —$(CH_2)_p$— group, in which p is 2 to 5, $R^5$ is hydrogen, $C_1$-$C_{10}$ alkyl, aryl, aralkyl, $CO_2H$, $CO_2$alkyl, $CH_2OH$, $CH_2O$alkyl, $CH_2O$acyl, CN, $CH_2NH_2$, $CH_2N(\text{alkyl, acyl})_{1,2}$, or $CH_2$Hal, Hal is a halogen atom, $R^6$, $R^7$, in each case, are hydrogen, or together an additional bond or together an oxygen atom, or together an NH group, or together an N-alkyl group, or together a $CH_2$ group, and G is an oxygen atom or $CH_2$, D-E is a group $H_2C$—$CH_2$, HC=CH, C≡C, CH(OH)—CH(OH), CH(OH)—$CH_2$, $CH_2$—CH(OH),

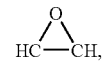

O—$CH_2$, or, if G represents a $CH_2$ group, is $CH_2$—O,

W is a group C(=X)$R^8$, or a bi- or tricyclic aromatic or heteroaromatic radical, $L^3$ is hydrogen, or, if a radical in W contains a hydroxyl group, forms a group O-$L^4$ with the latter, or, if a radical in W contains an amino group, forms a group $NR^{25}$-$L^4$ with the latter, $R^{25}$ is hydrogen or $C_1$-$C_{10}$ alkyl, X is an oxygen atom, or two $OR^{20}$ groups, or a $C_2$-$C_{10}$ alkylenedioxy group, which should be straight-chain or branched, or H/$OR^9$, or a $CR^{10}R^{11}$ group, $R^8$ is hydrogen, $C_1$-$C_{10}$ alkyl, aryl, aralkyl, halogen or CN, and $R^9$ is hydrogen or a protective group $PG^X$, $R^{10}$, $R^{11}$, in each case independently of one another, are hydrogen, $C_1$-$C_{20}$ alkyl, aryl, or aralkyl, or together with a methylene carbon atom form a 5- to 7-membered carbocyclic ring, Z can represent oxygen or H/OR$^{12}$, R$^{12}$ can represent hydrogen or a protective group PG$^Z$, A-Y can represent a group O—C(=O), O—CH$_2$, CH$_2$—C(=O), NR$^{21}$—C(=O) or NR$^{21}$—SO$_2$, R$^{20}$ can represent C$_1$-C$_{20}$ alkyl, R$^{21}$ can represent a hydrogen atom or C$_1$-C$_{10}$ alkyl, L$^1$, L$^2$, L$^4$, independently of one another, can represent hydrogen, a group C(=O)Cl, a group C(=S)Cl, a group PG$^Y$ or a linker-recognition unit of general formula III; with the condition that at least one substituent L$^1$, L$^2$ or L$^4$ represents a linker-recognition unit of general formula (III);

the linker-recognition unit of general formula (III) has the following structure,

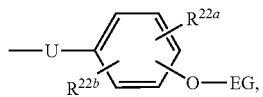

III in which

R$^{22a}$, R$^{22b}$, independently of one another, can represent hydrogen, C$_1$-C$_{20}$ alkyl, C$_1$-C$_{20}$ acyl, C$_1$-C$_{20}$ acyloxy, aryl, aralkyl, hydroxy, alkoxy, CO$_2$H, CO$_2$alkyl, halogen, CN, NO$_2$, NH$_2$, or N$_3$, U can represent —C(=O)NR$^{23}$—, —C(=S)NR$^{23}$—, —C(=O)NR$^{23}$—CH$_2$—, —C(=S)NR$^{23}$—CH$_2$—, —C(=O)O—, —C(=S)O—, —C(=O)O—CH$_2$—, —C(=S)O—CH$_2$—, R$^{23}$ can represent hydrogen or C$_1$-C$_{10}$ alkyl, and EG is a recognition unit of general formula IV,

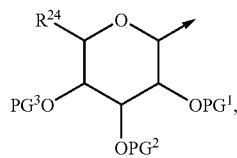

IV in which

R$^{24}$ can represent a group CH$_2$ OPG$^4$ or a group CO$_2$R$^{26}$,

PG$^1$, PG$^2$, PG$^3$, and PG$^4$, independently of one another, can represent hydrogen or a protective group PG, R$^{26}$ can represent hydrogen, C$_1$-C$_{20}$ alkyl, C$_1$-C$_{20}$ alkenyl, C$_4$-C$_7$ cycloalkyl, which can contain an oxygen atom, aryl, aralkyl, tris(C$_1$-C$_{20}$ alkyl)silyl, bis(C$_1$-C$_{20}$ alkyl)-arylsilyl, (C$_1$-C$_{20}$ alkyl)-diarylsilyl, or tris(aralkyl)-silyl, PG$^X$, PG$^Y$, and PG$^Z$ can represent a protective group PG, as a uniform isomer or a mixture of different isomers and/or as a pharmaceutically acceptable salt thereof.

According to this invention, the above-mentioned conjugates can comprise one or more recognition units; in this case, the recognition units that are related to a conjugate can be identical or different. It is preferred that the recognition units of a conjugate be identical.

The compounds of general formula I can be used in the form of their α-, β- or γ-cyclodextrin clathrates or their substituted α-, β- or γ-cyclodextrin clathrates or in the form of liposomal or PEGylated compositions.

The conjugates according to the invention are preferably used for the treatment of diseases that are linked to proliferative processes. For example, the therapy of widely varying tumors, the therapy of inflammatory and/or neurodegenerative diseases, such as multiple sclerosis or Alzheimer's disease, the therapy of angiogenesis-associated diseases, such as the growth of solid tumors, rheumatoid arthritis or diseases of the ocular fundus can be mentioned.

Especially preferred is the use of the conjugates according to the invention for the treatment of primary tumors and/or metastases that are not operatively accessible, either as monotherapy or in combination with substances that increasingly trigger cell death (apoptosis) and necrosis, so that when cells decompose, it results in an elevated release of normally intracellular, lysosomal enzymes, such as, e.g., glucuronidase, which results in a stronger reaction of the conjugates according to the invention. For example, in this connection, substances that are used for the so-called "vascular targeting" can be mentioned. These substances result in destruction in particular of the tumor endothelium, which subsequently results in an increased necrosis of the tumor because of the deficient nutrient supply. For example, L19 constructs, such as, for example, the EDB fibronectin or combrestatin A4-prodrugs, can be mentioned here.

The production of epothilones, their precursors and derivatives of general formula II is carried out according to the methods that are known to one skilled in the art, as they are described in, for example, DE 19907588, WO 98/25929, WO 99/58534, WO 99/2514, WO 99/67252, WO 99/67253, WO 99/7692, EP 99/4915, WO 00/485, WO 00/1333, WO 00/66589, WO 00/49019, WO 00/49020, WO 00/49021, WO 00/71521, WO 00/37473, WO 00/57874, WO 01/92255, WO 01/81342, WO 01/73103, WO 01/64650, WO 01/70716, U.S. Pat. Nos. 6,204,388, 6,387,927, 6,380,394, U.S. Ser. No. 02/52028, 02/58286, 02/62030, WO 02/32844, WO 02/30356, WO 02/32844, WO 02/14323, and WO 02/8440.

As alkyl groups R$^{1a}$, R$^{1b}$, R$^{2a}$, R$^{2b}$, R$^3$, R$^{4a}$, R$^{4b}$, R$^5$, R$^8$, R$^{10}$, R$^{11}$, R$^{20}$R$^{21}$, R$^{22a}$, R$^{22b}$, R$^{23}$, R$^{25}$, R$^{26}$ and R$^{27}$, straight-chain or branched-chain alkyl groups with 1-20 carbon atoms can be considered, such as, for example, methyl, ethyl, propyl, isopropyl, butyl, isobutyl, tert.-butyl, pentyl, isopentyl, neopentyl, heptyl, hexyl, and decyl.

Alkyl groups R$^{1a}$, R$^{1b}$, R$^{2a}$, R$^{2b}$, R$^3$, R$^{4a}$, R$^{4b}$, R$^5$, R$^8$, R$^{10}$, R$^{11}$, R$^{20}$, R$^{21}$, R$^{22a}$, R$^{22b}$, R$^{25}$, R$^{26}$ and R$^{27}$ can also be perfluorinated or substituted by 1-5 halogen atoms, hydroxy groups, C$_1$-C$_4$-alkoxy groups, or C$_6$-C$_{12}$-aryl groups (which can be substituted by 1-3 halogen atoms).

As aryl radicals R$^{1a}$, R$^{1b}$, R$^{2a}$, R$^{2b}$, R$^3$, R$^{4a}$, R$^{4b}$, R$^5$, R$^8$, R$^{10}$, R$^{11}$, R$^{22a}$, R$^{22b}$, R$^{26}$ and R$^{27}$, substituted and unsubstituted carbocyclic or heterocyclic radicals with one or more heteroatoms, such as phenyl, naphthyl, furyl, thienyl, pyridyl, pyrazolyl, pyrimidinyl, oxazolyl, pyridazinyl, pyrazinyl, quinolyl, thiazolyl, benzothiazolyl, benzoxazolyl, which can be substituted in one or more places by halogen, OH, O-alkyl, CO$_2$H, CO$_2$-alkyl, —NH$_2$, —NO$_2$, —N$_3$, —CN, C$_1$-C$_{20}$-alkyl, C$_1$-C$_{20}$-acyl, C$_1$-C$_{20}$-acyloxy groups, are suitable. The heteroatoms can be oxidized if as a result the aromatic character is not lost, such as, for example, the oxidation of a pyridyl to a pyridyl-N-oxide.

As bi- and tricyclic aryl radicals W, substituted and unsubstituted carbocyclic or heterocyclic radicals with one or more heteroatoms, such as naphthyl, anthryl, benzothiazolyl, benzoxazolyl, benzimidazolyl, quinolyl, isoquinolyl, benzoxazinyl, benzofuranyl, indolyl, indazolyl, quinoxalinyl, tetrahydroisoquinolinyl, tetrahydroquinolinyl, thienopyridinyl, pyridopyridinyl, benzopyrazolyl, benzotriazolyl, or dihydroindolyl, which can be substituted in one or more places by halogen, OH, O-alkyl, $CO_2H$, $C_2$-alkyl, $-NH_2$, $-NO_2$, $-N_3$, $-CN$, $C_1$-$C_{20}$-alkyl, $C_1$-$C_{20}$-acyl, or $C_1$-$C_{20}$-acyloxy groups, are suitable. The heteroatoms can be oxidized if as a result the aromatic character is not lost, such as, for example, the oxidation of a quinolyl to a quinolyl-N-oxide.

The aralkyl groups in $R^{1a}$, $R^{1b}$, $R^{2a}$, $R^{2b}$, $R^3$, $R^{4a}$, $R^{4b}$, $R^5$, $R^8$, $R^{10}$, $R^{11}$, $R^{22a}$, $R^{22b}$, $R^{26}$ and $R^{27}$ can contain in the ring up to 14 C atoms, preferably 6 to 10 C atoms, and in the alkyl chain 1 to 8, preferably 1 to 4 atoms. As aralkyl radicals, for example, benzyl, phenylethyl, naphthylmethyl, naphthylethyl, furylmethyl, thienylethyl, and pyridylpropyl are considered. The rings can be substituted in one or more places by halogen, OH, O-alkyl, $CO_2H$, $CO_2$-alkyl, $-NO_2$, $-N_3$, $-CN$, $C_1$-$C_{20}$-alkyl, $C_1$-$C_{20}$-acyl, or $C_1$-$C_{20}$-acyloxy groups.

As representatives of protective groups PG, tris($C_1$-$C_{20}$ alkyl)silyl, bis($C_1$-$C_{20}$ alkyl)-arylsilyl, ($C_1$-$C_{20}$ alkyl)-diarylsilyl, tris(aralkyl)-silyl, $C_1$-$C_{20}$-alkyl, $C_2$-$C_{20}$-alkenyl, $C_4$-$C_7$-cycloalkyl, which in addition can contain an oxygen atom in the ring, aryl, $C_7$-$C_{20}$-aralkyl, $C_1$-$C_{20}$-acyl, aroyl, $C_1$-$C_{20}$-alkoxycarbonyl, $C_1$-$C_{20}$-alkylsulfonyl as well as arylsulfonyl can be mentioned.

As alkyl, silyl and acyl radicals for protective groups PG, in particular the radicals that are known to one skilled in the art are considered. Preferred are the alkyl or silyl radicals that are easily cleavable from the corresponding alkyl ethers and silyl ethers, such as, for example, the methoxymethyl, methoxyethyl, ethoxyethyl, tetrahydropyranyl, tetrahydrofuranyl, trimethylsilyl, triethylsilyl, tert.-butyldimethylsilyl, tert.-butyldiphenylsilyl, tribenzylsilyl, triisopropylsilyl, benzyl, para-nitrobenzyl, or para-methoxybenzyl radical as well as alkylsulfonyl and arylsulfonyl radicals. As an alkoxycarbonyl radical, e.g., trichloroethyloxycarbonyl (Troc) is suitable. As acyl radicals, e.g., formyl, acetyl, propionyl, isopropionyl, trichloromethylcarbonyl, pivalyl, butyryl or benzoyl, which can be substituted with amino groups and/or hydroxy groups, are suitable.

As amino protective groups PG, the radicals that are known to one skilled in the art are considered. For example, the Alloc, Boc, Z, benzyl, f-Moc, Troc, Stabase or benzostabase group can be mentioned.

As halogen atoms, fluorine, chlorine, bromine or iodine is considered.

The acyl groups can contain 1 to 20 carbon atoms, whereby formyl, acetyl, propionyl, isopropionyl and pivalyl groups are preferred.

The $C_2$-$C_{10}$-alkylene-$\alpha,\omega$-dioxy group that is possible for X is preferably an ethyleneketal or neopentylketal group.

As preferred recognition units EG, those are considered that, for example, by overexpression of suitable enzymes in proliferating tissues can be cleaved from the latter. For example, glucuronidase can be mentioned here.

Preferred compounds of general formula I are those in which A-Y represents O—C(=O) or $NR^{21}$—C(=O); D-E represents an $H_2C$—$CH_2$ group or an HC=CH group; G represents a $CH_2$ group; Z represents an oxygen atom; $R^{1a}$, $R^{1b}$ in each case represent $C_1$-$C_{10}$ alkyl or together a —$(CH_2)_p$ group with p equal to 2 or 3 or 4; $R^{2a}$, $R^{2b}$, independently of one another, represent hydrogen, $C_1$-$C_{10}$ alkyl, $C_2$-$C_{10}$ alkenyl, or $C_2$-$C_1$ alkinyl; $R^3$ represents hydrogen; $R^{4a}$, $R^{4b}$, independently of one another, represent hydrogen or $C_1$-$C_{10}$ alkyl; $R^5$ represents hydrogen or $C_1$-$C_4$ alkyl or $CH_2OH$ or $CH_2NH_2$ or $CH_2N$(alkyl, acyl)$_{1,2}$ or $CH_2Hal$; $R^6$ and $R^7$ together represent an additional bond or together an oxygen atom or together an NH group or together an N-alkyl group or together a $CH_2$ group; W represents a group C(=X) or $R^8$ or a 2-methylbenzothiazol-5-yl radical or a 2-methylbenzoxazol-5-yl radical or a quinolin-7-yl radical or a 2-aminomethylbenzothiazol-5-yl radical or a 2-hydroxymethylbenzothiazol-5-yl radical or a 2-aminomethylbenzoxazol-5-yl radical or a 2-hydroxymethyl-benzoxazol-5-yl radical; X represents a $CR^{10}R^{11}$ group; $R^8$ represents hydrogen or $C_1$-$C_4$ alkyl or a fluorine atom or a chlorine atom or a bromine atom; $R^{10}/R^{11}$ represent hydrogen/2-methylthiazol-4-yl or hydrogen/2-pyridyl or hydrogen/2-methyloxazol-4-yl or hydrogen/2-aminomethylthiazol-4-yl or hydrogen/2-aminomethyloxazol-4-yl or hydrogen/2-hydroxymethylthiazol-4-yl or hydrogen/2-hydroxymethyloxazol-4-yl.

In a preferred embodiment, radicals $R^{22a}$ and $R^{22b}$ are selected from the group that consists of $C_1$-$C_8$-alkyl, $C_1$-$C_8$-alkoxy, halogen, nitro, CN, $N_3$, $NH_2$ and $CO_2$-($C_1$-$C_8$-alkyl). Especially preferred in this connection are the radicals methyl, ethyl, propyl, i-propyl, t-butyl, $CF_3$, $C_2F_5$, F, Cl, nitro, CN, $N_3$, $NH_2$, $CO_2$-methyl, $CO_2$-ethyl, $CO_2$-propyl and $CO_2$-i-propyl.

In another preferred embodiment, radical $R^{26}$ is selected from the group that consists of $C_1$-$C_8$-alkyl and $C_2$-$C_8$-alkenyl. Especially preferred in this connection are the radicals methyl, ethyl, propyl, i-propyl, t-butyl, $CF_3$, propenyl and butenyl.

In another preferred embodiment, radicals $R^{2a}$ and $R^{2b}$ are selected such that one of radicals $R^{2a}$ or $R^{2b}$ represents hydrogen, while the other radical in each case is selected from the group that consists of $C_1$-$C_7$-alkyl, $C_2$-$C_7$-alkenyl and $C_2$-$C_7$-alkinyl. Especially preferred in this connection are the radicals methyl, ethyl, propyl, i-propyl, propenyl, butenyl, propinyl and butinyl.

The compounds that are mentioned below are especially preferred according to the invention as effector elements:

(4S,7R,8S,9S,13Z,16S(E))-4,8-Dihydroxy-5,5,7,9,13-pentamethyl-16-[1-methyl-2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-1-methyl-vinyl]-5,5,7,9,13-pentamethyl-oxacyclohexadec-13-ene-2,6-dione;

(4S,7R,8S,9S,13Z,16S(E))-16-[2-(2-Aminomethyl-thiazol-4-yl)-1-methyl-vinyl]-4,8-dihydroxy-5,5,7,9,13-pentamethyl-oxacyclohexadec-13-ene-2,6-dione;

(1S,3S(E),7S,10R,11S,12S,16R)-7,11-Dihydroxy-8,8,10,12,16-pentamethyl-3-[1-methyl-2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-1-methyl-vinyl]-8,8,10,12,16-pentamethyl-4,17-dioxa-bicyclo[14.1.0]-heptadecane-5,9-dione;

(1S,3S(E),7S,10R,11S,12S,16R)-3-[2-(2-Aminomethyl-thiazol-4-yl)-1-methyl-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(E))-4,8-Dihydroxy-7-ethyl-5,5,9,13-tetramethyl-16-[1-methyl-2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-1-methyl-vinyl]-7-ethyl-5,5,9,13-tetramethyl-oxacyclohexadec-13-ene-2,6-dione;

(4S,7R,8S,9S,13Z,16S(E))-16-[2-(2-Aminomethyl-thiazol-4-yl)-1-methyl-vinyl-]4,8-dihydroxy-7-ethyl-5,5,9,13-tetramethyl-oxacyclohexadec-13-ene-2,6-dione;

(1S,3S(E),7S,10R,11S,12S,16R)-7,11-Dihydroxy-10-ethyl-8,8,12,16-tetramethyl-3-[1-methyl-2-(2-methyl-thiazol-4-yl)-vinyl]-4,17-dioxa-bicyclo[14.1.0]-heptadecane-5,9-dione;

(1S,3S(E),7S,10R,11S,12S,16R)-7,11-Dihydroxy-3-[2-(2-hydroxymethyl-thiazol-4-yl)-1-methyl-vinyl]-10-ethyl-8,8,12,16-tetramethyl-4,17-dioxa-bicyclo[14.1.0]heptadecane-5,9-dione;

(1S,3S(E),7S,10R,11S,12S,16R)-3-[2-(2-Aminomethyl-thiazol-4-yl)-1-methyl-vinyl]-7,11-dihydroxy-10-ethyl-8,8,12,16-tetramethyl-4,17-dioxa-bicyclo[14.1.0]-heptadecane-5,9-dione;

(4S,7R,8S,9S,13Z,16S(Z))-4,8-Dihydroxy-5,5,7,9,13-pentamethyl-16-[1-fluro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-fluoro-vinyl]-5,5,7,9,13-pentamethyl-oxacyclohexadec-13-ene-2,6-dione;

(4S,7R,8S,9S,13Z,16S(Z))-16-[2-(2-Aminomethyl-thiazol-4-yl)-1-fluro-viyl]-4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-fluoro-2-(2-methyl-thiazol-4-yl)-vinyl]-4,17-dioxa-bicyclo[14.1.0]-heptadecane-5,9-dione;

(1S,3S(Z),7S,10R,11S,12S,16R)-7,11-Dihydroxy-3-[2-(2-hydroxymethyl-thiazol-4-yl)-1-fluoro-vinyl]-8,8,10,12,16-pentamethyl-4,17-dioxa-bicyclo[14.1.0]-heptadecane-5,9-dione;

(1S,3S(Z),7S,10R,11S,12S,16R)-3-[2-(2-Aminomethyl-thiazol-4-yl)-1-fluoro-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(Z))-4,8-Dihydroxy-5,5,7,9,13-pentamethyl-16-[1-chloro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-chloro-vinyl]-5,5,7,9,13-pentamethyl-oxacyclohexadec-13-ene-2,6-dione;

(4S,7R,8S,9S,13Z,16S(Z))-16-[2-(2-Aminomethyl-thiazol-4-yl)-1-chloro-vinyl-]4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-chloro-2-(2-methyl-thiazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-thiazol-4-yl)-1-chloro-vinyl]-8,8,10,12,16-pentamethyl-4,17-dioxa-bicyclo[14.1.0]-heptadecane-5,9-dione;

(1S,3S(Z),7S,10R,11S,12S,16R)-3-[2-(2-Aminomethyl-thiazol-4-yl)-1-chloro-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(Z))-4,8-Dihydroxy-7-ethyl-5,5,9,13-tetramethyl-16-[1-fluoro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-fluoro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-thiazol-4-yl)-1-fluoro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-fluoro-2-(2-methyl-thiazol-4-yl)-vinyl]-4,17-dioxa-bicyclo[14.1.0]-heptadecane-5,9-dione;

(1S,3S(Z),7S,10R,11S,12S,16R)-7,11-Dihydroxy-3-[2-(2-hydroxymethyl-thiazol-4-yl)-1-fluoro-vinyl]-10-ethyl-8,8,12,16-tetramethyl-4,17-dioxa-bicyclo[14.1.0]heptadecane-5,9-dione;

(1S,3S(Z),7S,10R,11S,12S,16R)-3-[2-(2-Aminomethyl-thiazol-4-yl)-1-fluoro-vinyl]-7,11-dihydroxy-10-ethyl-8,8,12,16-tetramethyl-4,17-dioxa-bicyclo[14.1.0]-heptadecane-5,9-dione;

(4S,7R,8S,9S,13Z,16S(Z))-4,8-Dihydroxy-7-ethyl-5,5,9,13-tetramethyl-16-[1-chloro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-chloro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-thiazol-4-yl)-1-chloro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-chloro-2-(2-methyl-thiazol-4-yl)-vinyl]-4,17-dioxa-bicyclo[14.1.0]-heptadecane-5,9-dione;

(1S,3S(Z),7S,10R,11S,12S,16R)-7,11-Dihydroxy-3-[2-(2-hydroxymethyl-thiazol-4-yl)-1-chloro-vinyl]-10-ethyl-8,8,12,16-tetramethyl-4,17-dioxa-bicyclo[14.1.0]heptadecane-5,9-dione;

(1S,3S(Z),7S,10R,11S,12S,16R)-3-[2-(2-Aminomethyl-thiazol-4-yl)-1-chloro-vinyl]-7,11-dihydroxy-10-ethyl-8,8,12,16-tetramethyl-4,17-dioxa-bicyclo[14.1.0]-heptadecane-5,9-dione;

(4S,7R,8S,9S,13Z,16S(E))-4,8-Dihydroxy-5,5,7,9,13-pentamethyl-16-[1-methyl-2-(2-pyridyl)-vinyl]-oxacyclohexadec-13-ene-2,6-dione;

(1S,3S(E),7S,10R,11S,12S,16R)-7,11-Dihydroxy-8,8,10,12,16-pentamethyl-3-[1-methyl-2-(2-pyridyl)-vinyl]-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[1-methyl-2-(2-pyridyl)-vinyl]-oxacyclohexadec-13-ene-2,6-dione;

(1S,3S(E),7S,10R,11S,12S,16R)-7,11-Dihydroxy-10-ethyl-8,8,12,16-tetramethyl-3-[1-methyl-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-fluoro-2-(2-pyridyl)-vinyl]-oxacyclohexadec-13-ene-2,6-dione;

(1S,3S(Z),7S,10R,11S,12S,16R)-7,11-Dihydroxy-8,8,10,12,16-pentamethyl-3-[1-fluoro-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-chloro-2-(2-pyridyl)-vinyl]-oxacyclohexadec-13-ene-2,6-dione;

(1S,3S(Z),7S,10R,11S,12S,16R)-7,11-Dihydroxy-8,8,10,12,16-pentamethyl-3-[1-chloro-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-7-ethyl-5,5,9,13-tetramethyl-16-[1-fluoro-2-(2-pyridyl)-vinyl]-oxacyclohexadec-13-ene-2,6-dione;

(1S,3S(Z),7S,10R,11S,12S,16R)-7,11-Dihydroxy-10-ethyl-8,8,12,16-tetramethyl-3-[1-fluoro-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-7-ethyl-5,5,9,13-tetramethyl-16-[1-chloro-2-(2-pyridyl)-vinyl]-oxacyclohexadec-13-ene-2,6-dione;

(1S,3S(Z),7S,10R,11S,12S,16R)-7,11-Dihydroxy-10-ethyl-8,8,12,16-tetramethyl-3-[1-chloro-2-(2-pyridyl)-vinyl]-4,17-dioxa-bicyclo[14.1.0]heptadecane-5,9-dione;

(4S,7R,8S,9S,13Z,16S(E))-4,8-Dihydroxy-5,5,7,9,13-pentamethyl-16-[1-methyl-2-(2-methyl-oxazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-oxazol-4-yl)-1-methyl-vinyl]-5,5,7,9,13-pentamethyl-oxacyclohexadec-13-ene-2,6-dione;

(4S,7R,8S,9S,13Z,16S(E))-16-[2-(2-Aminomethyl-oxazol-4-yl)-1-methyl-vinyl-]-4,8-dihydroxy-5,5,7,9,13-pentamethyl-oxacyclohexadec-13-ene-2,6-dione;

(1S,3S(E),7S,10R,11S,12S,16R)-7,11-Dihydroxy-8,8,10,12,16-pentamethyl-3-[1-methyl-2-(2-methyl-oxazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-oxazol-4-yl)-1-methyl-vinyl]-8,8,10,12,16-pentamethyl-4,17-dioxa-bicyclo[14.1.0]-heptadecane-5,9-dione;

(1S,3S(E),7S,10R,11S,12S,16R)-3-[2-(2-Aminomethyl-oxazol-4-yl)-1-methyl-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(E))-4,8-Dihydroxy-7-ethyl-5,5,9,13-tetramethyl-16-[1-methyl-2-(2-methyl-oxazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-oxazol-4-yl)-1-methyl-vinyl]-7-ethyl-5,5,9,13-tetramethyl-oxacyclohexadec-13-ene-2,6-dione;

(4S,7R,8S,9S,13Z,16S(E))-16-[2-(2-Aminomethyl-oxazol-4-yl)-1-methyl-vinyl]-4,8-dihydroxy-7-ethyl-5,5,9,13-tetramethyl-oxacyclohexadec-13-ene-2,6-dione;

(1S,3S(E),7S,10R,11S,12S,16R)-7,11-Dihydroxy-10-ethyl-8,8,12,16-tetramethyl-3-[1-methyl-2-(2-methyl-oxazol-4-yl)-vinyl]-4,17-dioxa-bicyclo[14.1.0]-heptadecane-5,9-dione;

(1S,3S(E),7S,10R,11S,12S,16R)-7,11-Dihydroxy-3-[2-(2-hydroxymethyl-oxazol-4-yl)-1-methyl-vinyl]-10-ethyl-8,8,12,16-tetramethyl-4,17-dioxa-bicyclo[14.1.0]heptadecane-5,9-dione;

(1S,3S(E),7S,10R,11S,12S,16R)-3-[2-(2-Aminomethyl-oxazol-4-yl)-1-methyl-vinyl-]7,11-dihydroxy-10-ethyl-8,8,12,16-tetramethyl-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-fluoro-2-(2-methyl-oxazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-oxazol-4-yl)-1-fluoro-vinyl]-5,5,7,9,13-pentamethyl-oxacyclohexadec-13-ene-2,6-dione;

(4S,7R,8S,9S,13Z,16S(Z))-16-[2-(2-Aminomethyl-oxazol-4-yl)-1-fluoro-vinyl-]4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-fluoro-2-(2-methyl-oxazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-oxazol-4-yl)-1-fluoro-vinyl]-8,8,10,12,16-pentamethyl-4,17-dioxa-bicyclo[14.1.0]-heptadecane-5,9-dione;

(1S,3S(Z),7S,10R,11S,12S,16R)-3-[2-(2-Aminomethyl-oxazol-4-yl)-1-fluoro-vinyl-]7,11-dihydroxy-8,8,10,12,16-pentamethyl-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-chloro-2-(2-methyl-oxazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-oxazol-4-yl)-1-chloro-vinyl]-5,5,7,9,13-pentamethyl-oxacyclohexadec-13-ene-2,6-dione;

(4S,7R,8S,9S,13Z,16S(Z))-16-[2-(2-Aminomethyl-oxazol-4-yl)-1-chloro-vinyl]-4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-chloro-2-(2-methyl-oxazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-oxazol-4-yl)-1-chloro-vinyl]-8,8,10,12,16-pentamethyl-4,17-dioxa-bicyclo[14.1.0]-heptadecane-5,9-dione;

(1S,3S(Z),7S,10R,11S,12S,16R)-3-[2-(2-Aminomethyl-oxazol-4-yl)-1-chloro-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(Z))-4,8-Dihydroxy-7-ethyl-5,5,9,13-tetramethyl-16-[1-fluoro-2-(2-methyl-oxazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-oxazol-4-yl)-1-fluoro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-oxazol-4-yl)-1-fluoro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-fluoro-2-(2-methyl-oxazol-4-yl)-vinyl]-4,17-dioxa-bicyclo[14.1.0]-heptadecane-5,9-dione;

(1S,3S(Z),7S,10R,11S,12S,16R)-7,11-Dihydroxy-3-[2-(2-hydroxymethyl-oxazol-4-yl)-1-fluoro-vinyl]-10-ethyl-8,8,12,16-tetramethyl-4,17-dioxa-bicyclo[14.1.0]heptadecane-5,9-dione;

(1S,3S(Z),7S,10R,11S,12S,16R)-3-[2-(2-Aminomethyl-oxazol-4-yl)-1-fluoro-vinyl]-7,11-dihydroxy-10-ethyl-8,8,12,16-tetramethyl-4,17-dioxa-bicyclo [14.1.0]-heptadecane-5,9-dione;

(4S,7R,8S,9S,13Z,16S(Z))-4,8-Dihydroxy-7-ethyl-5,5,9,13-tetramethyl-16-[1-chloro-2-(2-methyl-oxazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-oxazol-4-yl)-1-chloro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-oxazol-4-yl)-1-chloro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-chloro-2-(2-methyl-oxazol-4-yl)-vinyl]-4,17-dioxa-bicyclo[14.1.0]-heptadecane-5,9-dione;

(1S,3S(Z),7S,10R,11S,12S,16R)-7,11-Dihydroxy-3-[2-(2-hydroxymethyl-oxazol-4-yl)-1-chloro-vinyl]-10-ethyl-8,8,12,16-tetramethyl-4,17-dioxa-bicyclo[14.1.0]-heptadecane-5,9-dione;

(1S,3S(Z),7S,10R,11S,12S,16R)-3-[2-(2-Aminomethyl-oxazol-4-yl)-1-chloro-vinyl]-7,11-dihydroxy-10-ethyl-8,8,12,16-tetramethyl-4,17-dioxa-bicyclo[14.1.0]-heptadecane-5,9-dione;

(4S,7R,8S,9S,13Z,16S(E))-4,8-Dihydroxy-5,5,7,9,13-pentamethyl-16-[2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-vinyl]-5,5,7,9,13-pentamethyl-oxacyclohexadec-13-ene-2,6-dione;

(4S,7R,8S,9S,13Z,16S(E))-16-[2-(2-Aminomethyl-thiazol-4-yl)-vinyl]-4,8-dihydroxy-5,5,7,9,13-pentamethyl-oxacyclohexadec-13-ene-2,6-dione;

(1S,3S(E),7S,10R,11S,12S,16R)-7,11-Dihydroxy-8,8,10,12,16-pentamethyl-3-[2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-vinyl]-8,8,10,12,16-pentamethyl-4,17-dioxa-bicyclo[14.1.0]heptadecane-5,9-dione;

(1S,3S(E),7S,10R,11S,12S,16R)-3-[2-(2-Aminomethyl-thiazol-4-yl)-vinyl]-7,11-dihydroxy-8,8,10,12,16-pentamethyl-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-vinyl]-7-ethyl-5,5,9,13-tetramethyl-oxacyclohexadec-13-ene-2,6-dione;

(4S,7R,8S,9S,13Z,16S(E))-16-[2-(2-Aminomethyl-thiazol-4-yl)-vinyl]-4,8-dihydroxy-7-ethyl-5,5,9,13-tetramethyl-oxacyclohexadec-13-ene-2,6-dione;

(1S,3S(E),7S,10R,11S,12S,16R)-7,11-Dihydroxy-10-ethyl-8,8,12,16-tetramethyl-3-[2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-vinyl]-10-ethyl-8,8,12,16-tetramethyl-4,17-dioxa-bicyclo[14.1.0]-heptadecane-5,9-dione;

(1S,3S(E),7S,10R,11S,12S,16R)-3-[2-(2-Aminomethyl-thiazol-4-yl)-vinyl]-7,11-dihydroxy-10-ethyl-8,8,12,16-tetramethyl-4,17-dioxa-bicyclo[14.1.0]heptadecane-5,9-dione;

(4S,7R,8S,9S,13Z,16S(E))-4,8-Dihydroxy-5,5,7,9,13-pentamethyl-16-[2-(2-pyridyl)-vinyl]-oxacyclohexadec-13-ene-2,6-dione;

(1S,3S(E),7S,10R,11S,12S,16R)-7,11-Dihydroxy-8,8,10,12,16-pentamethyl-3-[2-(2-pyridyl)-vinyl]-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[2-(2-pyridyl)-vinyl]-oxacyclohexadec-13-ene-2,6-dione;

(1S,3S(E),7S,10R,11S,12S,16R)-7,11-Dihydroxy-10-ethyl-8,8,12,16-tetramethyl-3-[2-(2-pyridyl)-vinyl]-4,17-dioxa-bicyclo[14.1.0]heptadecane-5,9-dione;

(4S,7R,8S,9S,13Z,16S)-4,8-Dihydroxy-5,5,7,9,13-pentamethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-5,5,7,9,13-pentamethyl-oxacyclohexadec-13-ene-2,6-dione;

(4S,7R,8S,9S,13Z,16S)-16-(2-Aminomethyl-benzothiazol-5-yl)-4,8-dihydroxy-5,5,7,9,13-pentamethyl-oxacyclohexadec-13-ene-2,6-dione;

(1S,3S,7S,10R,11S,12S,16R)-7,11-Dihydroxy-8,8,10,12,16-pentamethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-8,8,10,12,16-pentamethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-8,8,10,12,16-pentamethyl-4,17-dioxa-bicyclo[14.1.0]heptadecane-5,9-dione;

(4S,7R,8S,9S,13Z,16S)-4,8-Dihydroxy-7-ethyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-ethyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-ethyl-5,5,9,13-tetramethyl-oxacyclohexadec-13-ene-2,6-dione;

(1S,3S,7S,10R,11S,12S,16R)-7,11-Dihydroxy-10-ethyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-ethyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-ethyl-8,8,12,16-tetramethyl-4,17-dioxa-bicyclo[14.1.0]heptadecane-5,9-dione;

(4S,7R,8S,9S,13Z,16S)-4,8-Dihydroxy-7-propyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-propyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-propyl-5,5,9,13-tetramethyl-oxacyclohexadec-13-ene-2,6-dione;

(1S,3S,7S,10R,11S,12S,16R)-7,11-Dihydroxy-10-propyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-propyl-8,8,12,16-tetramethyl-4,17-dioxa-bicyclo[14.1.0]-heptadecane-5,9-dione;

(1S,3S,7S,10R,11S,12S,16R)-3-(2-Arninomethyl-benzothiazol-5-yl)-7,11-dihydroxy-10-propyl-8,8,12,16-tetramethyl-4,17-dioxa-bicyclo[14.1.0]heptadecane-5,9-dione;

(4S,7R,8S,9S,13Z,16S)-4,8-Dihydroxy-7-butyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-butyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-butyl-5,5,9,13-tetramethyl-oxacyclohexadec-13-ene-2,6-dione;

(1S,3S,7S,10R,11S,12S,16R)-7,11-Dihydroxy-10-butyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-butyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-butyl-8,8,12,16-tetramethyl-4,17-dioxa-bicyclo[14.1.0]heptadecane-5,9-dione;

(4S,7R,8S,9S,13Z,16S)-4,8-Dihydroxy-7-allyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-allyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-allyl-5,5,9,13-tetramethyl-oxacyclohexadec-13-ene-2,6-dione;

(1S,3S,7S,10R,11S,12S,16R)-7,11-Dihydroxy-10-allyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-allyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-allyl-8,8,12,16-tetramethyl-4,17-dioxa-bicyclo[14.1.0]heptadecane-5,9-dione;

(4S,7R,8S,9S,13Z,16S)-4,8-Dihydroxy-7-prop-2-inyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-prop-2-inyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-prop-2-inyl-5,5,9,13-tetramethyl-oxacyclohexadec-13-ene-2,6-dione;

(1S,3S,7S,10R,11S,12S,16R)-7,11-Dihydroxy-10-prop-2-inyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-prop-2-inyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-prop-2-inyl-8,8,12,16-tetramethyl-4,17-dioxa-bicyclo[14.1.0]-heptadecane-5,9-dione;

(4S,7R,8S,9S,13Z,16S)-4,8-Dihydroxy-7-but-3-enyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-but-3-enyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-but-3-enyl-5,5,9,13-tetramethyl-oxacyclohexadec-13-ene-2,6-dione;

(1S,3S,7S,10R,11S,12S,16R)-7,11-Dihydroxy-10-but-3-enyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-but-3-enyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-but-3-enyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-inyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-but-3-inyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-but-3-inyl-5,5,9,13-tetramethyl-oxacyclohexadec-13-ene-2,6-dione;

(1S,3S,7S,10R,11S,12S,16R)-7,11-Dihydroxy-10-but-3-inyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-but-3-inyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-but-3-inyl-8,8,12,16-tetramethyl-4,17-dioxa-bicyclo[14.1.0]heptadecane-5,9-dione;

(4S,7R,8S,9S,13Z,16S)-4,8-Dihydroxy-5,5,7,9,13-pentamethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-5,5,7,9,13-pentamethyl-oxacyclohexadec-13-ene-2,6-dione;

(4S,7R,8S,9S,13Z,16S)-16-(2-Aminomethyl-benzoxazol-5-yl)-4,8-dihydroxy-5,5,7,9,13-pentamethyl-oxacyclohexadec-13-ene-2,6-dione;

(1S,3S,7S,10R,11S,12S,16R)-7,11-Dihydroxy-8,8,10,12,16-pentamethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-8,8,10,12,16-pentamethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-8,8,10,12,16-pentamethyl-4,17-dioxa-bicyclo[14.1.0]heptadecane-5,9-dione;

(4S,7R,8S,9S,13Z,16S)-4,8-Dihydroxy-7-ethyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-ethyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-ethyl-5,5,9,13-tetramethyl-oxacyclohexadec-13-ene-2,6-dione;

(1S,3S,7S,10R,11S,12S,16R)-7,11-Dihydroxy-10-ethyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-ethyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-ethyl-8,8,12,16-tetramethyl-4,17-dioxa-bicyclo[14.1.0]heptadecane-5,9-dione;

(4S,7R,8S,9S,13Z,16S)-4,8-Dihydroxy-7-propyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-propyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-propyl-5,5,9,13-tetramethyl-oxacyclohexadec-13-ene-2,6-dione;

(1S,3S,7S,10R,11S,12S,16R)-7,11-Dihydroxy-10-propyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-propyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-propyl-8,8,12,16-tetramethyl-4,17-dioxa-bicyclo[14.1.0]heptadecane-5,9-dione;

(4S,7R,8S,9S,13Z,16S)-4,8-Dihydroxy-7-butyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-butyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-butyl-5,5,9,13-tetramethyl-oxacyclohexadec-13-ene-2,6-dione;

(1S,3S,7S,10R,11S,12S,16R)-7,11-Dihydroxy-10-butyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-butyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-butyl-8,8,12,16-tetramethyl-4,17-dioxa-bicyclo [14.1.0]heptadecane-5,9-dione;

(4S,7R,8S,9S,13Z,16S)-4,8-Dihydroxy-7-allyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-allyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-allyl-5,5,9,13-tetramethyl-oxacyclohexadec-13-ene-2,6-dione;

(1S,3S,7S,10R,11S,12S,16R)-7,11-Dihydroxy-10-allyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-allyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-allyl-8,8,12,16-tetramethyl-4,17-dioxa-bicyclo[14.1.0]heptadecane-5,9-dione;

(4S,7R,8S,9S,13Z,16S)-4,8-Dihydroxy-7-prop-2-inyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-prop-2-inyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-prop-2-inyl-5,5,9,13-tetramethyl-oxacyclohexadec-13-ene-2,6-dione;

(1S,3S,7S,10R,11S,12S,16R)-7,11-Dihydroxy-10-prop-2-inyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-prop-2-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-prop-2-inyl-8,8,12,16-tetramethyl-4,17-dioxa-bicyclo[14.1.0]-heptadecane-5,9-dione;

(4S,7R,8S,9S,13Z,16S)-4,8-Dihydroxy-7-but-3-enyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-but-3-enyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-but-3-enyl-5,5,9,13-tetramethyl-oxacyclohexadec-13-ene-2,6-dione;

(1S,3S,7S,10R,11S,12S,16R)-7,11-Dihydroxy-10-but-3-enyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-but-3-enyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-but-3-enyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-inyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-but-3-inyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-but-3-inyl-5,5,9,13-tetramethyl-oxacyclohexadec-13-ene-2,6-dione;

(1S,3S,7S,10R,11S,12S,16R)-7,11-Dihydroxy-10-but-3-inyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-but-3-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-but-3-inyl-8,8,12,16-tetramethyl-4,17-dioxa-bicyclo[14.1.0]heptadecane-5,9-dione.

In a compound of general formula (I) according to the invention that contains one of the above-mentioned elements, the hydrogen atoms in the above-mentioned elements are replaced by radicals $L^1$-$L^3$ in the positions indicated in formula (I), whereby radicals $L^1$-$L^3$ have the above-indicated meanings.

The invention also relates to linker-recognition units of general formula $III^1$:

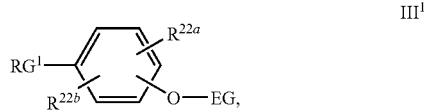

in which

RG$^1$ represents an O=C=N group or an S=C=N group or an O=C=N—CH$_2$ group or an S=C=N—CH$_2$ group; and $R^{22a}$, $R^{22b}$ and EG have the above-indicated meanings;

as well as linker-recognition units of general formula $III^2$:

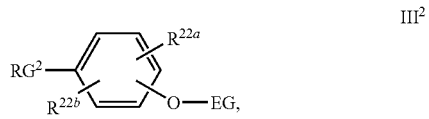

in which

RG$^2$ represents an HO—CH$_2$ group or an HNR$^{23}$—CH$_2$ group; and $R^{22a}$, $R^{22b}$ and EG have the above-mentioned meanings;

but with the condition that the following compounds are not included:

(4-Hydroxymethyl)phenyl-2,3,4,6-tetra-O-acetyl-α-D-galactopyranoside;

(2-Hydroxymethyl)phenyl-2,3,4,6-tetra-O-acetyl-α-D-galactopyranoside;

(4-Hydroxymethyl)phenyl-2,3,4-tri-O-acetyl-β-D-glucuronide-6-methyl ester;

(2-Hydroxymethyl)phenyl-2,3,4-tri-O-acetyl-β-D-glucuronide-6-methyl ester;

(4-Hydroxymethyl)phenyl-2,3,4,6-tetra-O-acetyl-β-D-glucopyranoside;

(2-Hydroxymethyl-4-nitro)phenyl-2,3,4,6-tetra-O-acetyl-α-D-galactopyranoside;

(4-Hydroxymethyl-2-nitro)phenyl-2,3,4,6-tetra-O-acetyl-α-D-galactopyranoside;

(2-Hydroxymethyl-4-nitro)phenyl-2,3,4-tri-O-acetyl-β-D-glucuronide-6-methyl ester;

(4-Hydroxymethyl-2-nitro)phenyl-2,3,4-tri-O-acetyl-β-D-glucuronide-6-methyl ester;

(2-Chloro-4-hydroxymethyl)phenyl-2,3,4,6-tetra-O-acetyl-α-D-galactopyranoside;

(2-Chloro-4-hydroxyrethyl)phenyl-2,3,4-tri-O-acetyl-β-D-glucuronide-6-methyl ester;

as well as linker-recognition units of general formula III³:

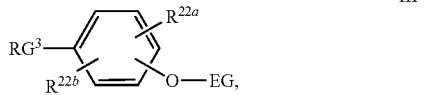

in which

RG³ represents a Hal-C(=O)—CH₂ group or a Hal-C(=S)—CH₂ group or an R²⁷—C(=O)—O—C(=O)—CH₂ group or an R²⁷—C(=O)—O—C(=S)—CH₂ group or a

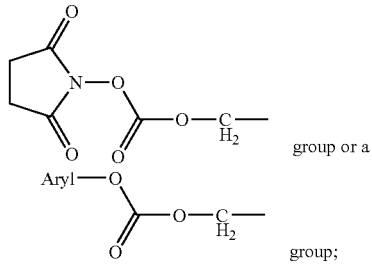

group or a group;

$R^{27}$ is $C_1$-$C_{10}$ alkyl, aryl or aralkyl; and $R^{22a}$, $R^{22b}$ and EG have the above-mentioned meanings;

but with the condition that the following compounds are not included:

2,5-Dioxopyrrolidin-1-yl-[4-(2,3,4,6-tetra-O-acetyl-α-D-galactopyranosyl)-benzyl]carbonate;

2,5-Dioxopyrrolidin-1-yl-[2-(2,3,4,6-tetra-O-acetyl-α-D-galactopyranosyl)-benzyl]carbonate;

2,5-Dioxopyrrolidin-1-yl-[4-((2,3,4-tri-O-acetyl-β-D-glucopyranosyl)-methyluronate)benzyl]carbonate;

4-Nitrophenyl-[2-((2,3,4-tri-O-acetyl-β-D-glucopyranosyl)methyluronate)-benzyl]carbonate;

2,5-Dioxopyrrolidin-1-yl-[4-(2,3,4,6-tetra-O-acetyl-β-D-glucopyranosyl)benzyl]-carbonate;

4-Nitrophenyl-[2-(2,3,4,6-tetra-O-acetyl-α-D-galactopyranosyl)-5-nitrobenzyl]-carbonate;

4-Nitrophenyl-[2-((2,3,4-tri-O-acetyl-β-D-glucopyranosyl)methyluronate)-5-nitrobenzyl]carbonate;

4-Nitrophenyl-[4-methoxy-5-nitro-2-((2,3,4-tri-O-acetyl-β-D-glucopyranosyl)methyluronate)benzyl]carbonate;

4-Nitrophenyl-[4-((2,3,4-tri-O-acetyl-β-D-glucopyranosyl)methyluronate)-5-nitrobenzyl]carbonate;

4-Chlorophenyl-[2-((2,3,4-tri-O-acetyl-β-D-glucopyranosyl)methyluronate)-5-nitrobenzyl]carbonate.

The invention also relates to processes for reacting a linker-recognition unit of general formula III¹ with a compound of general formula I, in which the condition that at least one group $L^1$, $L^2$ or $L^4$ represent a linker-recognition unit need not be met, and $L^1$ and/or $L^2$ and/or $L^4$ have the meaning of a hydrogen atom, and free hydroxyl groups and/or amino groups that are not required for the reaction optionally are protected, for reacting a linker-recognition unit of general formula III² with a compound of general formula I, in which the condition that at least one group $L^1$, $L^2$ or $L^4$ represent a linker-recognition unit need not be met, and $L^1$ and/or $L^2$ and/or $L^4$ have the meaning of a C(=O)Hal group or a C(=S)Hal group, and free hydroxyl groups and/or amino groups that are not required for the reaction are optionally protected, for reacting a linker-recognition unit of general formula III³ with a compound of general formula I, in which the condition that at least one group $L^1$, $L^2$ or $L^4$ represent a linker-recognition unit need not be met, and $L^1$ and/or $L^2$ and/or $L^4$ have the meaning of a hydrogen atom, and free hydroxyl groups and/or amino groups that are not required for the reaction are optionally protected.

The invention also relates to the use of a compound of general formula I, whereby the substituents have the above-mentioned meanings, but the condition that at least one substituent $L^1$, $L^2$ or $L^4$ represent a linker of general formula III need not be met, and at least one substituent $L^1$, $L^2$ or $L^4$ represents hydrogen, a group C(=O)Cl, or a group C(S)Cl, in a process as described above.

The invention also relates to the use of a compound of general formula I, whereby the substituents have the above-mentioned meanings, but the condition that at least one substituent $L^1$, $L^2$ or $L^4$ represent a linker of general formula III need not be met, and at least one substituent $L^1$, $L^2$ or $L^4$ represents hydrogen, a group C(=O)Cl, or a group C(S)Cl, for the production of an effector recognition unit conjugate as described above.

The invention also relates to the use of a linker-recognition unit of general formula III¹, III² or III³ for the production of an effector-recognition unit conjugate, as described above.

The invention also relates to the use of a linker-recognition unit of general formula III¹, III² or III³ in one of the processes according to the invention for the production of an effector-recognition unit conjugate as described above.

The invention also relates to the conjugates according to the invention that contain effectors, linkers and recognition units for use as medications or for the production of a medication or a pharmaceutical composition.

The invention also relates to the use of the conjugates according to the invention for the production of medications for the treatment of diseases that are linked to proliferative processes, such as tumors, inflammatory and/or neurodegenerative diseases, multiple sclerosis, Alzheimer's disease, or for the treatment of angiogenesis-associated diseases, such as the growth of solid tumors, rheumatoid arthritis, or diseases of the ocular fundus.

The invention also relates to the use of the conjugates according to the invention for the production of medications for the treatment of primary tumors and/or metastases that are not operatively accessible, either as monotherapy or in combination with substances that increasingly trigger cell death (apoptosis) and necrosis, so that when tumor cells decompose, it results in an elevated release of normally intracellular, lysosomal enzymes, such as, e.g., glucuronidase, which results in a stronger reaction of the above-mentioned conjugates.

Treatment or administration in combination with the above-mentioned substances in this case comprises the simultaneous (both in the mixture and in separate doses) but also the respectively separate administration of the individual components of the combination, for example an alternating administration, as well as administration schemes, in which one component is given as a long-term medication, and the other component is administered in addition at regular or irregular intervals for shorter periods. In this case, the components of the combination can be fed via the same or via different administration paths. In the above-mentioned administrations in combination are preferably those in which the components of the combination achieve an additive action; especially preferred are those administration schemes in which a synergistic action is set.

With respect to a combination administration with the conjugates according to the invention, for example, substances can be mentioned that are used for the so-called "vascular targeting." These substances result in destruction especially of tumor endothelium, which subsequently results in an elevated necrosis of the tumor because of the deficient supply of nutrients. For example, L19 constructs, such as, for example the EDB-fibronectin or combrestatin A4-prodrugs, can be mentioned here.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES OF THE SYNTHESIS OF LINKER-RECOGNITION UNITS (LE)

Example LE1

(2S,3S,4S,5R,6S)-3,4,5-Triacetoxy-6-(4-hydroxymethyl-2-nitro-phenoxy)-tetrahydro-pyran-2-carboxylic acid methyl ester Example LE1a (2S,3S,4S,5R,6S)-3,4,5-Triacetoxy-6-(4-formyl-2-nitro-phenoxy)-tetrahydro-pyran-2-carboxylic acid methyl ester The solution of 5.0 g (12.6 mmol) of (2S,3S,4S,5R,6S)-3,4,5-triacetoxy-6-bromo-tetrahydro-pyran-2-carboxyclic acid methyl ester in 90 ml of acetonitrile is mixed with 2.1 g of 4-hydroxy-3-nitrobenzaldehyde, 3.58 g of silver(I) oxide, and it is stirred for 16 hours at 23° C. It is filtered over Celite, and the residue that is obtained after removal of the solvent is purified by chromatography on fine silica gel. 5.72 g (11.8 mmol, 94%) of the title compound is isolated.

Example LE1

(2S,3S,4S,5R,6S)-3,4,5-Triacetoxy-6-(4-hydroxymethyl-2-nitro-phenoxy)-tetrahydro-pyran-2-carboxylic acid methyl ester The solution of 5.72 g (11.8 miol) of the compound, presented according to Example LE1a, in a mixture that consists of 110 ml of tetrahydrofuran and 22 ml of methanol is mixed at 0° C. with 224 mg of sodium borohydride, and it is stirred for 30 minutes. It is mixed with saturated ammonium chloride solution, diluted with water and extracted several times with ethyl acetate. The combined organic extracts are washed with saturated sodium chloride solution, dried on sodium sulfate, and the residue that is obtained after filtration and removal of the solvent is purified by chromatography on fine silica gel. 5.62 g (11.6 mmol, 98%) of the title compound is isolated.

$^1$H-NMR (d$_6$-DMSO): δ=1.99+2.02 (9H), 3.64 (3H), 4.51 (2H), 4.73 (1H), 5.07 (1H), 5.12 (1H), 5.43 (1H), 5.48 (1H), 5.71 (1H), 7.38 (1H), 7.62 (1H), 7.80 (1) ppm.

Example LE2

(2S,3S,4S,5R,6S)-3,4,5-Triacetoxy-6-(2-hydroxymethyl-4-nitro-phenoxy)-tetrahydro-pyran-2-carboxylic acid methyl ester Example LE2a (2S,3S,4S,5R,6S)-3,4,5-Triacetoxy-6-(2-formyl-4-nitro-phenoxy)-tetrahydro-pyran-2-carboxylic acid methyl ester Analogously to Example LE1a, 5.0 g (12.6 mmol) of (2S,3S,4S,5R,6S)-3,4,5-triacetoxy-6-bromo-tetrahydro-pyran-2-carboxylic acid methyl ester is reacted with 2-hydroxy-3-nitrobenzaldehyde, and after working-up and purification, 4.31 g (8.92 mmol, 71%) of the title compound is isolated.

Example LE2

(2S,3S,4S,5R,6S)-3,4,5-Triacetoxy-6-(2-hydroxymethyl-4-nitro-phenoxy)-tetrahydro-pyran-2-carboxylic acid methyl ester Analogously to Example LE1, 1.0 g (2.07 mmol) of the compound that is presented according to Example LE2a is reacted, and after working-up and purification, 921 mg (1.90 mmol, 92%) of the title compound is isolated.

$^1$H-NMR (CDCl$_3$): δ=2.06 (3H), 2.08 (3H), 2.10 (3H), 2.53 (1H), 3.71 (3H), 4.25 (1H), 4.61 (1H), 4.72 (1H), 5.27-5.44 (4H), 7.09 (1H), 8.18 (1H), 8.30 (1) ppm.

Example LE3

(2S,3S,4S,5R,6S)-3,4,5-Tris-(tert-butyl-dimethyl-silanyloxy)-6-(2-hydroxymethyl-4-nitro-phenoxy)-tetrahydro-pyran-2-carboxylic acid allyl ester Example LE3a 2-[1,3]Dioxolan-2-yl-4-nitro-phenol The solution of 25 g (149.6 mmol) of 2-hydroxy-5-nitrobenzaldehyde in 500 ml of toluene is mixed with 100 ml of ethylene glycol, 2.85 g of p-toluenesulfonic acid monohydrate, and it is refluxed in a water separator for 5 hours. After cooling, it is poured into saturated sodium bicarbonate solution, extracted several times with ethyl acetate, the combined organic extracts are washed with saturated sodium chloride solution and dried on sodium sulfate. The residue that is obtained after filtration and removal of the solvent is further reacted without being purified.

Example LE3b (2S,3S,4S,5R,6S)-3,4,5-Triacetoxy-6-(2-[1,3]dioxolan-2-yl-4-nitro-phenoxy)-tetrahydro-pyran-2-carboxylic acid methyl ester 20.0 g (50.4 mmol) of (2S,3S,4S,5R,6S)-3,4,5-triacetoxy-6-bromo-tetrahydro-pyran-2-carboxylic acid methyl ester is reacted analogously to Example LE1a with the compound that is presented according to Example LE3a, and after working-up and purification, 21.9 g (41.5 mmol, 82%) of the title compound is isolated.

Example LE3c (2S,3S,4S,5R,6S)-6-(2-[1,3]Dioxolan-2-yl-4-nitro-phenoxy)-3,4,5-trihydroxy-tetrahydro-pyran-2-carboxylic acid methyl ester The solution of 21.85 g (41.5 mmol) of the compound, presented according to Example LE3b, in 1.17 l of methanol is mixed at 0° C. with the solution of 2.42 g of sodium methanolate in 45 ml of methanol, and it is stirred for 3 more hours. It is mixed with 9.14 g of citric acid hydrate and concentrated by evaporation. The residue is dissolved in a mixture that consists of ethyl acetate and methanol, filtered over a short silica gel layer, and16.6 g (41.4 mmol, 99%) of the title compound is isolated after removal of the solvent.

Example LE3d (2S,3S,4S,5R,6S)-3,4,5-Tris-(tert-butyl-dimethyl-silanyloxy)-6-(2-[1,3]dioxolan-2-yl-4-nitro-phenoxy)-tetrahydro-pyran-2-carboxylic acid methyl ester The solution of 8.0 g (19.9 mmol) of the compound, presented according to Example LE3c, in 560 ml of dichloromethane, is mixed with 22.9 ml of tert-butyl-dimethyl-silyltriflate as well as 23.8 ml of 2,6-lutidine, and it is stirred for 24 hours at 23° C. It is poured into water, extracted several times with dichloromethane, the combined organic extracts are washed with saturated sodium chloride solution and dried on magnesium sulfate. The residue that is obtained after filtration and removal of the solvent is purified by chromatography on fine silica gel, and 9.90 g (13.3 mmol, 67%) of the title compound as well as 2.17 g (29.2 mmol, 15%) of a stereoisomer are isolated.

Example LE3e (2S,3S,4S,5R,6S)-3,4,5-Tris-(tert-butyl-dimethyl-silanyloxy)-6-(2-[1,3]dioxolan-2-yl-4-nitro-phenoxy)-tetrahydro-pyran-2-carboxylic acid The solution of 5.64 g (7.58 mmol) of the compound, presented according to Example LE3d, in 150 ml of allyl alcohol is mixed with 9.1 ml of a 1 M solution of sodium allyl alcoholate in allyl alcohol, and it is stirred for 2.5 hours at 50° C. It is concentrated by evaporation, mixed with water, extracted several times with dichloromethane, the combined organic extracts are washed with saturated sodium chloride solution and dried on magnesium sulfate. The residue that is obtained after filtration and removal of the solvent is purified by chromatography on fine silica gel, and 1.78 g (2.44 mmol, 32%) of the title compound as well as 1.87 g (2.43 mmol, 32%) of (2R,3S,4S,5R,6S)-3,4,5-tris-(tert-butyl-dimethyl-silanyloxy)-6-(2-[1,3]dioxolan-2-yl-4-nitro-phenoxy)-tetrahydro-pyran-2-carboxylic acid allyl ester are isolated.

Example LE3f (2S,3S,4S,5R,6S)-3,4,5-Tris-(tert-butyl-dimethyl-silanyloxy)-6-(2-[1,3]dioxolan-2-yl4-nitro-phenoxy)-tetrahydro-pyran-2-carboxylic acid allyl ester The solution of 1.35 g (1.85 mmol) of the compound, presented according to Example LE3e, in 5 ml of dimethylformamide is mixed with 0.3 ml of 1,8-diazabicyclo[5.4.0]undec-7-ene as well as 0.176 ml of allyl bromide, and it is stirred for 16 hours at 23° C. It is poured into water, extracted several times with ethyl acetate, the combined organic extracts are washed with saturated sodium chloride solution and dried on magnesium sulfate. The residue that is obtained after filtration and removal of the solvent is purified by chromatography on fine silica gel, and 1.03 g (1.34 mmol, 72%) of the title compound is isolated.

Example LE3g (2S,3S,4S,5R,6S)-3,4,5-Tris-(tert-butyl-dimethyl-silanyloxy)-6-(2-formyl-4-nitro-phenoxy)-tetrahydro-pyran-2-carboxylic acid allyl ester The solution of 50 mg (61.6 µmol) of the compound, presented according to Example LE3f, in 2 ml of acetone is mixed with 12.9 mg of p-toluenesulfonic acid monohydrate, and it is stirred for 24 hours at 23° C. It is poured into saturated sodium bicarbonate solution, extracted several times with ethyl acetate, the combined organic extracts are washed with saturated sodium chloride solution and dried on magnesium sulfate. The residue that is obtained after filtration and removal of the solvent is purified by chromatography on fine silica gel, and 25.9 mg (35.7 µmol, 58%) of the title compound is isolated.

Example LE3

(2S,3S,4S,5R,6S)-3,4,5-Tris-(tert-butyl-dimethyl-silanyloxy)-6-(2-hydroxymethyl-4-nitro-phenoxy)-tetrahydro-pyran-2-carboxylic acid allyl ester 720 mg (0.99 mmol) of the compound that is presented according to Example LE3g is reacted analogously to Example LE1, and after working-up, 710 mg (0.975 mmol, 98%) of the title compound, which is further reacted without being purified, is isolated.

$^1$H-NMR (CDCl$_3$): δ=0.05-0.15 (18H), 0.85-0.94 (27H), 2.97 (1H), 3.87 (1H), 3.99 (1H), 4.36 (1H), 4.41 (1H), 4.52 (1H), 4.58 (2H), 5.01 (1H), 5.22 (1H), 5.28 (1H), 5.61 (1H), 5.85 (1H), 7.07 (1H), 8.18 (1H), 8.33 (1H) ppm.

Example LE4

(2S,3S,4S,5R,6S)-3,4,5-Tris-(tert-butyl-dimethyl-silanyloxy)-6-(4-hydroxymethyl-2-nitro-phenoxy)-tetrahydro-pyran-2-carboxylic acid allyl ester Example LE4a 4-[1,3]Dioxolan-2-yl-2-nitro-phenol Analogously to Example LE3a, 25 g (149.6 mmol) of 4-hydroxy-3-nitrobenzaldehyde is reacted, and after working-up, 27.6 g (131 mmol, 87%) of the title compound is isolated.

Example LE4b (2S,3S,4S,5R,6S)-3,4,5-Triacetoxy-6-(4-[1,3]dioxolan-2-yl-2-nitro-phenoxy)-tetrahydro-pyran-2-carboxylic acid methyl ester 23.4 g (59.0 mmol) of (2S,3S,4S,5R,6S)-3,4,5-triacetoxy-6-bromo-tetrahydro-pyran-2-carboxylic acid methyl ester is reacted analogously to Example LE1a with the compound that is presented according to Example LE4a, and after working-up and purification, 24.5 g (46.4 mmol, 79%) of the title compound is isolated.

Example LE4c (2S,3S,4S,5R,6S)-6-(4-[1,3]Dioxolan-2-yl-2-nitro-phenoxy)-3,4,5-trihydroxy-tetrahydro-pyran-2-carboxylic acid methyl ester 358 mg (679 µmol) of the compound that is presented according to Example LE4b is reacted analogously to Example LE3c, and after working-up, 270 mg (673 µmol, 99%) of the title compound is isolated.

Example LE4d (2S,3S,4S,5R,6S)-3,4,5-Tris-(tert-butyl-dimethyl-silanyloxy)-6-(4-[1,3]dioxolan-2-yl-2-nitro-phenoxy)-tetrahydro-pyran-2-carboxylic acid methyl ester 268 mg (668 µmol) of the compound that is presented according to Example LE4c is reacted analogously to Example LE3d, and after working-up and purification, 183 mg (246 µmol, 37%) of the title compound is isolated.

Example LE4e (2S,3S,4S,5R,6S)-3,4,5-Tris-(tert-butyl-dimethyl-silanyloxy)-6-(4-[1,3]dioxolan-2-yl-2nitro-phenoxy)-tetrahydro-pyran-2-carboxylic acid The solution of 5.0 g (6.72 mmol) of the compound, presented according to Example LE4d, in 130 ml of methanol is mixed with 3.6 ml of water, heated to 70° C. and mixed with 3.01 ml of 1,8-diazabicyclo[5.4.0]undec-7-ene. It is allowed to react for 4 more hours, set at a pH of 3 by adding 1N hydrochloric acid, and extracted several times with ethyl acetate. The combined organic extracts are washed with water and saturated sodium chloride solution and dried on sodium sulfate. The residue that is obtained after filtration and removal of the solvent is purified by chromatography on fine silica gel, and 1.53 g (2.10 mmol, 31%) of the title compound is isolated.

Example LE4f (2S,3S,4S,5R,6S)-3,4,5-Tris-(tert-butyl-dimethyl-silanyloxy)-6-(4-[1,3]dioxolan-2-yl-2-nitro-phenoxy)-tetrahydro-pyran-2-carboxylic acid allyl ester 2.87 g (3.93 mmol) of the compound that is presented according to Example LE4e is reacted analogously to Example LE3f, and after working-up and purification, 2.51 g (3.26 mmol, 83%) of the title compound is isolated.

Example LE4g (2S,3S,4S,5R,6S)-3,4,5-Tris-(tert-butyl-dimethyl-silanyloxy)-6-(4-formyl-2-nitro-phenoxy)-tetrahydro-pyran-2-carboxylic acid allyl ester 2.51 g (3.26 mmol) of the compound that is presented according to Example LE4f is reacted analogously to Example LE3g, and after working-up, 2.35 g (3.24 mmol, 99%) of the title compound, which is further reacted without being purified, is isolated.

Example LE4

(2S,3S,4S,5R,6S)-3,4,5-Tris-(tert-butyl-dimethyl-silanyloxy)-6-(4-hydroxymethyl-2-nitro-phenoxy)-tetrahydro-pyran-2-carboxylic acid allyl ester 2.23 g (3.07 mmol) of the compound that is presented according to Example LE4g is reacted analogously to Example LE1, and after working-up and purification, 2.12 g (2.91 mmol, 95%) of the title compound is isolated.

$^1$H-NMR (CDCl$_3$): δ=0.00 (3H), 0.07 (3H), 0.12-0.17 (12H), 0.83 (9H), 0.87 (9H), 0.92 (9H), 1.83 (1H), 3.85 (1H), 4.05 (1H), 4.40 (1H), 4.51 (1H), 4.60 (2H), 4.70 (2H), 5.22 (1H), 5.30 (1H), 5.58 (1H), 5.87 (1H), 7.17 (1H), 7.52 (1H), 7.83 (1H) ppm.

Example LE5

(2S,3S,4S,5R,6S)-3,4,5-Tris-(tert-butyl-dimethyl-silanyloxy)-6-(4-hydroxymethyl-phenoxy)-tetrahydro-pyran-2-carboxylic acid allyl ester

Example LE5a (2S,3S,4S,5R,6S)-3,4,5-Triacetoxy-6-(4-formyl-phenoxy)-tetrahydro-pyran-2-carboxylic acid methyl ester 44.1 g (111 mmol) of (2S,3S,4S,5R,6S)-3,4,5-triacetoxy-6-bromo-tetrahydro-pyran-2-carboxylic acid methyl ester is reacted analogously to Example LE1a with 14 g of 4-hydroxy-benzaldehyde, and after working-up and purification, 35.1 g (80 mmol, 72%) of the title compound is isolated.

Example LE5b (2S,3S,4S,5R,6S)-3,4,5-Triacetoxy-6-(4-hydroxymethyl-phenoxy)-tetrahydro-pyran-2-carboxylic acid methyl ester 16.5 g (37.7 mmol) of the compound that is presented according to Example LE5a is reacted analogously to Example LE1, and after working-up, 17.4 g (max. 37.7 mmol) of the title compound, which is further reacted without being purified, is isolated.

Example LE5c (2S,3S,4S,5R,6S)-3,4,5-Trihydroxy-6-(4-hydroxymethyl-phenoxy)-tetrahydro-pyran-2-carboxylic acid methyl ester 17.4 g (max. 37.7 mmol) of the compound that is presented according to Example LE5b is reacted analogously to Example LE3c, and after working-up, 13.9 g (max. 37.7 mmol) of the title compound, which is further reacted without being purified, is isolated.

Example LE5d (2S,3S,4S,5R,6S)-3,4,5-Tris-(tert-butyl-dimethyl-silanyloxy)-6-(4-tert-butyl-dimethyl-silanyloxymethyl-phenoxy)-tetrahydro-pyran-2-carboxylic acid methyl ester 13.9 g (max. 37.7 mmol) of the compound that is presented according to Example LE5c is reacted analogously to Example LE3d, and after working-up and purification, 21.5 g (27.9 mmol, 74%) of the title compound is isolated.

Example LE5e (2S,3S,4S,5R,6S)-3,4,5-Tris-(tert-butyl-dimethyl-silanyloxy)-6-(4-tert-butyl-dimethyl-silanyloxymethyl-phenoxy)-tetrahydro-pyran-2-carboxylic acid allyl ester The solution of 21.5 g (27.9 mmol) of the compound, presented according to Example LE5d, in 103 ml of allyl alcohol is mixed with 9.9 ml of titanium(IV)-tetraisopropoxide, and it is heated for 21 hours under an atmosphere of dry argon to 110° C. After cooling, it is mixed with water, diluted with ethyl acetate, filtered over Celite, and the organic phase is separated. The aqueous phase is extracted several times with ethyl acetate, the combined organic extracts are washed with saturated sodium chloride solution, and it is dried on sodium sulfate. After filtration and removal of the solvent, 22.6 g (max. 27.9 mmol) of the title compound, which is further reacted without being purified, is isolated.

Example LE5

(2S,3S,4S,5R,6S)-3,4,5-Tris-(tert-butyl-dimethyl-silanyloxy)-6-(4-hydroxymethyl-phenoxy)-tetrahydro-pyran-2-carboxylic acid allyl ester The solution of 22.6 g (max. 27.9 mmol) of the compound, presented according to Example LE5e, in a mixture that consists of 445 ml of dichloromethane and 218 ml of methanol is mixed at 0° C. with 6.47 g of rac. camphor-10-sulfonic acid, and it is stirred for 1.5 hours at 0° C. It is mixed with a saturated sodium bicarbonate solution, diluted with water, extracted several times with dichloromethane, and the combined organic extracts are dried on sodium sulfate. After filtration, removal of the solvent and purification, 14.4 g (21.0 mmol, 75%) of the title compound is isolated.

$^1$H-NMR (CDCl$_3$): δ=−0.02 (3H), 0.07 (3H), 0.12 (3H), 0.14 (3H), 0.17 (6H), 0.85 (9H), 0.88 (9H), 0.92 (9H), 1.56 (1H), 3.86 (1H), 3.98 (1H), 4.37 (1H), 4.54 (1H), 4.62 (4H), 5.22 (1H), 5.31 (1H), 5.55 (1H), 5.89 (1H), 6.95 (2H), 7.28 (2H) ppm.

Example LE6

(2S,3S,4S,5R,6S)-4-Hydroxy-3,5-bis-triisopropylsilanyloxy-6-(4-hydroxymethyl-2-chloro-phenoxy)-tetrahydro-pyran-2-carboxylic acid allyl ester

Example LE6a

2-Chloro-4-[1,3]dioxolan-2-yl-phenol 25 g (160 mmol) of 3-chloro-4-hydroxybenzaldehyde is reacted analogously to Example LE3a, and after working-up, 26.1 g (130 mmol, 81%) of the title compound, which is further reacted without being purified, is isolated.

Example LE6b (2S,3S,4S,5R,6S)-6-(2-Chloro-4-[1,3]dioxolan-2-yl-phenoxy)-3,4,5-tris-acetoxy-tetrahydro-pyran-2-carboxylic acid methyl ester 29.1 g (73.3 mmol) of (2S,3S,4S,5R,6S)-3,4,5-triacetoxy-6-bromo-tetrahydro-pyran-2-carboxylic acid methyl ester is reacted analogously to Example LE1a with 14.9 g of the compound that is presented according to Example LE6a, and after working-up and purification, 11.7 g (22.6 mmol, 31%) of the title compound is isolated.

Example LE6c (2S,3S,4S,5R,6S)-6-(2-Chloro-4-[1,3]dioxolan-2-yl-phenoxy)-3,4,5-tris-hydroxy-tetrahydro-pyran-2-carboxylic acid methyl ester 25.3 g (48.9 mmol) of the compound that is presented according to Example LE6b is reacted analogously to Example LE3c, and after working-up, 17.2 g (44.0 mmol, 90%) of the title compound, which is further reacted without being purified, is isolated.

Example LE6d (2S,3S,4S,5R,6S)-6-(2-Chloro-4-[1,3]dioxolan-2-yl-phenoxy)-4-hydroxy-3,5-bis-triisopropylsilanyloxy-tetrahydro-pyran-2-carboxylic acid methyl ester 17.2 g (44.0 mmol) of the compound that is presented according to Example LE6c is reacted analogously to Example LE3d with use of trifluoromethanesulfonic acid-triisopropylsilylester, and after working-up and purification, 18.1 g (25.7 mmol, 58%) of the title compound is isolated.

Example LE6e (2S,3S,4S,5R,6S)-6-(2-Chloro-4-[1,3]dioxolan-2-yl-phenoxy)-4-hydroxy-3,5-bis-triisopropylsilanyloxy-tetrahydro-pyran-2-carboxylic acid The solution of 18.1 g (25.8 mmol) of the compound, presented according to Example LE6d, in 400 ml of methanol is mixed with 13.9 ml of water, 7.7 ml of 1,8-diazabicyclo[5.4.0]undec-7-ene, and it is stirred for 4 hours at 70° C. It is concentrated by evaporation, diluted with ethyl acetate and water, set at a pH of 2 with 4N hydrochloric acid, the separated organic phase is dried on sodium sulfate, and the residue that is obtained after filtration and removal of the solvent is purified by chromatography. 12.2 g (17.7 mmol, 69%) of the title compound is isolated.

Example LE6f (2S,3S,4S,5R,6S)-6-(2-Chloro-4-[1,3]dioxolan-2-yl-phenoxy)-4-hydroxy-3,5-bis-triisopropylsilanyloxy-tetrahydro-pyran-2-carboxylic acid allyl ester 12.2 g (17.7 mmol) of the compound that is presented according to Example LE6e is reacted analogously to Example LE3f, and after working-up and purification, 12.9 g (17.7 mmol, 100%) of the title compound is isolated.

Example LE6g (2S,3S,4S,5R,6S)-6-(2-Chloro-4-formyl-phenoxy)-4-hydroxy-3,5-bis-triisopropylsilanyloxy-tetrahydro-pyran-2-carboxylic acid allyl ester 12.9 g (17.7 mmol) of the compound that is presented according to Example LE6f is reacted analogously to Example LE3g, and after working-up, 12.0 g (17.5 mmol, 99%) of the title compound, which is further reacted without being purified, is isolated.

Example LE6

(2S,3S,4S,5R,6S)-4-Hydroxy-3,5-bis-triisopropylsilanyloxy-6-(4-hydroxymethyl-2-chloro-phenoxy)-tetrahydro-pyran-2-carboxylic acid allyl ester 12.0 g (17.5 mmol) of the compound, presented according to Example LE6f, is reacted analogously to Example LE1, and after working-up and purification,11.4 g (16.6 mmol, 95%) of the title compound is isolated.
$^1$H-NMR (CDCl$_3$): δ=0.98-1.31 (42H), 1.64 (1H), 2.43 (1H), 3.67 (1H), 4.03 (1H), 4.10 (1H), 4.26 (1H), 4.54-4.64 (4H), 5.16-5.31 (3H), 5.84 (1H), 7.02 (1H), 7.19 (1H), 7.39 (1H) ppm.

Example LE7

(2S,3S,4S,5R,6S)-3,4,5-Tris-(tert-butyl-dimethyl-silanyloxy)-6-(4-hydroxymethyl-2-methoxy-phenoxy)-tetrahydro-pyran-2-carboxylic acid allyl ester

Example LE7a (2S,3S,4S,5R,6S)-3,4,5-Triacetoxy-6-(4-formyl-2-methoxy-phenoxy)-tetrahydro-pyran-2-carboxylic acid methyl ester Variant 1
8.0 g (20.1 mmol) of (2S,3S,4S,5R,6S)-3,4,5-triacetoxy-6-bromo-tetrahydro-pyran-2-carboxylic acid methyl ester is reacted analogously to Example LE1a with 3.1 g of 4-hydroxy-3-methoxybenzaldehyde, and after working-up and purification, 3.2 g (6.8 mmol, 34%) of the title compound is isolated.

Variant 2
The solution of 5.0 g (12.6 mmol) of (2S,3S,4S,5R,6S)-3,4,5-triacetoxy-6-bromo-tetrahydropyran-2-carboxylic acid methyl ester in 150 ml of toluene is mixed with 20 g of 4-hydroxy-3-methoxybenzaldehyde, 30 ml of a 5N potassium hydroxide solution, 5.0 g of tetrabutylammonium hydrogen sulfate, and it is stirred for 2 days at 23° C. It is mixed with ethyl acetate and water, the organic phase is separated, and the aqueous phase is extracted several times with ethyl acetate. The combined organic extracts are washed with saturated sodium chloride solution, dried on sodium sulfate, and the residue that is obtained after filtration and removal of the solvent is purified by chromatography. 1.94 g (4.14 mmol, 33%) of the title compound is isolated.

Example LE7b (2S,3S,4S,5R,6S)-3,4,5-Triacetoxy-6-(4-hydroxymethyl-2-methoxy-phenoxy)-tetrahydropyran-2-carboxylic acid methyl ester 5.55 g (11.9 mmol) of the compound that is presented according to Example LE7a is reacted analogously to Example LE1, and after working-up and purification, 3.67 g (7.80 mmol, 66%) of the title compound is isolated.

Example LE7c (2S,3S,4S,5R,6S)-3,4,5-Trihydroxy-6-(4-hydroxymethyl-2-methoxy-phenoxy)-tetrahydro-pyran-2-carboxylic acid methyl ester 5.25 g (11.2 mmol) of the compound that is presented according to Example LE7b is reacted analogously to Example LE3c, and after working-up, 4.64 g (max. 11.2 mmol) of the title compound, which is further reacted without being purified, is isolated.

Example LE7d (2S,3S,4S,5R,6S)-3,4,5-Tris-(tert-butyl-dimethyl-silanyloxy)-6-(4-tert-butyl-dimethyl-silanyloxymethyl-2-methoxy-phenoxy)-tetrahydro-pyran-2-carboxylic acid methyl ester 4.64 g (max. 11.2 mmol) of the compound that is presented according to Example LE7c is reacted analogously to Example LE3d, and after working-up and purification, 8.43 g (10.5 mmol, 94%) of the title compound is isolated.

Example LE7e (2S,3S,4S,5R,6S)-3,4,5-Tris-(tert-butyl-dimethyl-silanyloxy)-6-(4-tert-butyl-dimethyl-silanyloxymethyl-2-methoxy-phenoxy)-tetrahydro-pyran-2-carboxylic acid allyl ester 8.43 g (10.5 mmol) of the compound that is presented according to Example LE7d is reacted analogously to Example LE5e, and after working-up, 8.38 g (10.1 mmol, 96%) of the title compound, which is further reacted without being purified, is isolated.

Example LE7

(2S,3S,4S,5R,6S)-3,4,5-Tris-(tert-butyl-dimethyl-silanyloxy)-6-(4-hydroxymethyl-2-methoxy-phenoxy)-tetrahydro-pyran-2-carboxylic acid allyl ester 8.38 g (10.1 mmol) of the compound that is presented according to Example LE7e is reacted analogously to Example LE5, and after working-up and purification, 5.92 g (8.3 mmol, 82%) of the title compound is isolated.

$^1$H-NMR (CDCl$_3$): δ=−0.04 (3H), 0.06 (3H), 0.12 (3H), 0.13 (3H), 0.16 (3H), 0.21 (3H), 0.84 (9H), 0.87 (9H), 0.92 (9H), 1.59 (1H), 3.82 (3H), 3.86 (1H), 4.01 (1H), 4.37 (1H), 4.52 (1H), 4.61 (4H), 5.21 (1H), 5.30 (1H), 5.52 (1H), 5.89 (1H), 6.83 (1H), 6.90 (1H), 6.92 (1H) ppm.

Example LE8

(2S,3S,4S,5R,6S)-3,4,5-Tris-(tert-butyl-dimethyl-silanyloxy)-6-(4-hydroxymethyl-2-fluoro-phenoxy)-tetrahydro-pyran-2-carboxylic acid allyl ester

Example LE8a (2S,3S,4S,5R,6S)-3,4,5-Triacetoxy-6-(4-formyl-2-fluoro-phenoxy)-tetrahydro-pyran-2-carboxylic acid methyl ester 14.2 g (35.8 mmol) of (2S,3S,4S,5R,6S)-3,4,5-triacetoxy-6-bromo-tetrahydro-pyran-2-carboxylic acid methyl ester is reacted analogously to Example LE1a with 5.05 g of 3-fluoro-4-hydroxybenzaldehyde, and after working-up and purification, 13.3 g (29.1 mmol, 81%) of the title compound is isolated.

Example LE8b (2S,3S,4S,5R,6S)-3,4,5-Triacetoxy-6-(4-hydroxymethyl-2-fluoro-phenoxy)-tetrahydro-pyran-2-carboxylic acid methyl ester 13.3 g (29.1 mmol) of the compound that is presented according to Example LE8a is reacted analogously to Example LE1, and after working-up, 13.3 g (29.0 mmol, 100%) of the title compound, which is further reacted without being purified, is isolated.

Example LE8c (2S,3S,4S,5R,6S)-3,4,5-Trihydroxy-6-(4-hydroxymethyl-2-fluoro-phenoxy)-tetrahydro-pyran-2-carboxylic acid methyl ester 11.2 g (29.0 mmol) of the compound that is presented according to Example LE8b is reacted analogously to Example LE3c, and after working-up, 11.2 g (max. 29.0 mmol) of the title compound, which is further reacted without being purified, is isolated.

Example LE8d (2S,3S,4S,5R,6S)-3,4,5-Tris-(tert-butyl-dimethyl-silanyloxy)-6-(4-tert-butyl-dimethyl-silanyloxymethyl-2-fluoro-phenoxy)-tetrahydro-pyran-2-carboxylic acid methyl ester 11.2 g (max. 29.0 mmol) of the compound that is presented according to Example LE8c is reacted analogously to Example LE3d, and after working-up and purification, 18.5 g (23.4 mmol, 81%) of the title compound is isolated.

Example LE8e (2S,3S,4S,5R,6S)-3,4,5-Tris-(tert-butyl-dimethyl-silanyloxy)-6-(4-tert-butyl-dimethyl-silanyloxymethyl-2-fluoro-phenoxy)-tetrahydro-pyran-2-carboxylic acid allyl ester 18.5 g (23.4 mmol) of the compound that is presented according to Example LE8d is reacted analogously to Example LE5e, and after working-up, 18.6 g (22.8 mmol, 97%) of the title compound, which is further reacted without being purified, is isolated.

Example LE8

(2S,3S,4S,5R,6S)-3,4,5-Tris-(tert-butyl-dimethyl-silanyloxy)-6-(4-hydroxymethyl-2-fluoro-phenoxy)-tetrahydro-pyran-2-carboxylic acid allyl ester 18.6 g (22.8 mmol) of the compound that is presented according to Example LE8e is reacted analogously to Example LE5, and after working-up and purification, 13.3 g (19.0 mmol, 83%) of the title compound is isolated.

$^1$H-NMR (CDCl$_3$): δ=−0.02 (3H), 0.07 (3H), 0.12 (3H), 0.13 (3H), 0.17 (3H), 0.19 (3H), 0.84 (9H), 0.88 (9H), 0.92 (9H), 1.62 (1H), 3.86 (1H), 4.01 (1H), 4.38 (1H), 4.53 (1H), 4.61 (4H), 5.22 (1H), 5.31 (1H), 5.55 (1H), 5.90 (1H), 7.00 (1H), 7.02 (1H), 7.10 (1H) ppm.

Examples Of The Synthesis Of Effector-Linker Recognition Units (ELE)

Example ELE1

(2S,3S,4S,5R,6S)-3,4,5-Triacetoxy-6-{4-[(4S,7R,8S,9S,13Z,16S)-7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenoxy}-tetrahydro-pyran-2-carboxylic acid methyl ester

Example ELE1a (4S,7R,8S,9S,13Z,16S)-7-Allyl-8-(tert-butyl-dimethyl-silanyloxy)-4-hydroxy-5,5,9,13-tetramethyl-16-(2-methyl-benzothiazol-5-yl)-oxacyclohexadec-13-ene-2,6-dione The solution of 6.0 g (7.93 mmol) of (4S,7R,8S,9S,13Z,16S)-7-allyl-4,8-bis(tert-butyl-dimethyl-silanyloxy)-5,5,9,13-tetramethyl-16-(2-methyl-benzothiazol-5-yl)-oxacyclohexadec-13-ene-2,6-dione, which was produced analogously to the process described in WO 00/66589, in 186 ml of anhydrous dichloromethane is mixed at 0° C. with 26.4 ml of a 20% solution of trifluoroacetic acid in dichloromethane, and it is stirred for 6 hours at 0° C. It is poured into saturated sodium bicarbonate solution, extracted with dichloromethane, the combined organic extracts are washed with water and dried on magnesium sulfate. The residue that is obtained after filtration and removal of the solvent is purified by chromatography on fine silica gel. 3.32 g (5.17 mmol, 65%) of the title compound is isolated as a colorless solid.

Example ELE1b (4S,7R,8S,9S,13Z,16S)-Chloroformic acid-7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yl ester The solution of 1.0 g (1.56 mmol) of the compound, presented according to Example ELE1a, in 20 ml of dichloromethane is mixed at 0° C. with the solution of 285 mg of triphosgene in 6 ml of dichloromethane, 160 µl of pyridine, and it is stirred for 2.5 hours at 23° C. It is concentrated by evaporation, the residue is taken up in ethyl acetate, washed with water and saturated sodium chloride solution, and dried on magnesium sulfate. The residue that is obtained after filtration and removal of the solvent is purified by chromatography on fine silica gel. 1.08 g (1.53 mmol, 98%) of the title compound is isolated.

Example ELE1c (2S,3S,4S,5R,6S)-3,4,5-Triacetoxy-6-{4-[(4S,7R,8S,9S,13Z,16S)7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-nitro-phenoxy}-tetrahydro-pyran-2-carboxylic acid methyl ester The solution of 1.08 g (1.53 mmol) of the compound, presented according to Example ELE1b, in 30 ml of dichloromethane is mixed with 4.0 g of the compound that is presented according to Example LE1, 277 µl of triethylamine, and the suspension is stirred for 16 hours at 23° C. It is filtered, concentrated by evaporation, and the residue is purified by chromatography on fine silica gel. 408 mg (354 µmol, 23%) of the title compound is isolated.

Example ELE1

(2S,3S,4S,5R,6S)-3,4,5-Triacetoxy-6-{4-[(4S,7R,8S,9S,13Z,16S)-7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenoxy}-tetrahydro-pyran-2-carboxylic acid methyl ester The solution of 400 mg (347 µmol) of the compound, presented according to Example ELE1c, in a mixture that consists of 4.2 ml of tetrahydrofuran and 4.2 ml of acetonitrile is mixed with 1.59 ml of hexafluorosilicic acid, 404 µl of trifluoroacetic acid, and it is stirred for 48 hours at 23° C. It is poured into saturated sodium bicarbonate solution, extracted several times with ethyl acetate, the combined organic extracts are washed with saturated sodium chloride solution and dried on sodium sulfate. The residue that is obtained after filtration and removal of the solvent is purified by chromatography on fine silica gel, and 61 mg (58.7 µmol, 17%) of the title compound is isolated.

$^1$H-NMR (CDCl$_3$): δ=0.95-1.90 (6H), 1.01 (3H), 1.14 (6H), 1.70 (3H), 206 (6H), 2.13 (3H), 2.19-2.56 (6H), 2.68 (1H), 2.76 (3H), 2.95 (1H), 3.39 (1H), 3.69 (1H), 3.74 (3H), 4.22 (1H), 4.51 (1H), 4.74 (1H), 4.99-5.38 (7H), 5.54 (1H), 5.71 (1H), 5.96 (1H), 7.21-7.28 (2H), 7.35 (1H), 7.48 (1H), 7.77 (1H), 7.93 (1H) ppm.

Example ELE2

(2S,3S,4S,5R,6S)-3,4,5-Triacetoxy-6-{4-[(1S,3S,7S,10R,11S,12S,16R)-10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenoxy}-tetrahydro-pyran-2-carboxylic acid methyl ester The solution of 61 mg (58.7 µmol) of the compound, presented according to Example ELE1, in 2 ml of dichloromethane is mixed at −50° C. with 1.2 ml of a 0.1 M solution of dimethyldioxiram in acetone, and it is stirred for 1 hour. It is poured into a semiconcentrated sodium thiosulfate solution, extracted several times with dichloromethane, and the combined organic extracts are washed on sodium sulfate. The residue that is obtained after filtration and removal of the solvent is purified by chromatography on analytical thin-layer plates. 29 mg (27.5 µmol, 47%) of the title compound as well as 10 mg (9.5 µmol, 16%) of (2S,3S,4S,5R,6S)-3,4,5-triacetoxy-6-{4-[(1R,3S,7S,10R,11S,12S,16S)-10-allyl-11-hydroxy-8,8,12,16-tetramethyl-3-(2-methyl-benzothiazol-5-yl)-5,9-dioxo-4,17-dioxa-bicyclo[14.1.0]heptadec-7-yloxycarbonyloxymethyl]-2-nitro-phenoxy}-tetrahydro-pyran-2-carboxylic acid methyl ester are isolated.

$^1$H-NMR (CDCl$_3$): δ=1.03 (3H), 1.13 (3H), 1.16 (3H), 1.31 (3H), 1.34-1.88 (7H), 2.06 (6H), 2.12 (3H), 2.16-2.57 (6H), 2.71 (1H), 2.79 (3H), 2.84 (1H), 3.44 (1H), 3.69 (1H), 3.73 (3H), 4.22 (1H), 4.50 (1H), 4.71 (1H), 4.99-5.05 (2H), 5.19 (1H), 5.25-5.39 (3H), 5.45 (1H), 5.75 (1H), 6.07 (1H), 7.27 (2H), 7.32 (1H), 7.53 (1H), 7.78 (1H), 7.89 (1H) ppm.

Example ELE3

(2S,3S,4S,5R,6S)-3,4,5-Triacetoxy-6-{2-[(4S,7R,8S,9S,13Z,16S)-7-allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-4-nitro-phenoxy}-tetrahydro-pyran-2-carboxylic acid methyl ester Example ELE3a (2S,3S,4S,SR,6S)-3,4,5-Triacetoxy-6-{2-[(4S,7R,8S,9S,13Z,16S)7-allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-4-nitro-phenoxy}-tetrahydro-pyran-2-carboxylic acid methyl ester Analogously to Example ELE1c, 265 mg (376 µmol) of the compound that is presented according to Example ELE1b is reacted with the compound that is presented according to Example LE1, and after working-up and purification, 180 mg (156 µmol, 42%) of the title compound is isolated.

Example ELE3

(2S,3S,4S,5R,6S)-3,4,5-Triacetoxy-6-{2-[(4S,7R,8S, 9S,13Z,16S)-7-allyl-8-hydroxy-5,5,9,13-tetramethyl-16-(2-methyl-benzothiazol-5-yl)-2,6-dioxo-oxacy-clohexadec-13-en-4-yloxycarbonyloxymethyl]-4-nitro-phenoxy}-tetrahydro-pyran-2-carboxylic acid methyl ester Analogously to Example ELE1, 173 mg (150 μmol) of the compound that is presented according to Example ELE3a is reacted, and after working-up and purification, 58 mg (55.8 μmol, 37%) of the title compound is isolated.

$^1$H-NMR (CDCl$_3$): δ=1.00 (3H), 1.12 (3H), 1.13 (3H), 1.02-2.55 (13H), 1.70 (3H), 2.04 (3H), 2.07 (6H), 2.68 (1H), 2.76 (3H), 2.97 (1H), 3.39 (1H), 3.71 (1H), 3.73 (3H), 4.25 (1H), 4.65 (1H), 4.84 (1H), 5.00 (1H), 5.04 (1H), 5.16-5.38 (5H), 5.51 (1H), 5.72 (1H), 5.97 (1H), 7.08 (1H), 7.35 (1H), 7.79 (1H), 7.92 (1H), 7.98 (1H) ppm.

Example ELE4

(2S,3S,4S,5R,6S)-3,4,5-Triacetoxy-6-{2-[(1S,3S,7S, 10R,11S,12S,16R)-10-allyl-11-hydroxy-8,8,12,16-tetramethyl-3-(2-methyl-benzothiazol-5-yl)-5,9-di-oxo-4,17-dioxa-bicyclo[14.1.0]heptadec-7-yloxycarbonyloxymethyl]-4-nitro-phenoxy}-tetrahydro-pyran-2-carboxylic acid methyl ester Analogously to Example ELE2, 151 mg (145 μmol) of the compound that is presented according to Example ELE3 is reacted, and after working-up and purification, 75 mg (71.1 μmol, 49%) of the title compound as well as 28 mg (26.5 μmol, 18%) of (2S,3S,4S,5R,6S)-3,4,5-triacetoxy-6-{2-[(1R,3S,7S,10R,11S,12S,16S)-10-allyl-11-hydroxy-8,8, 12,16-tetramethyl-3-(2-methyl-benzothiazol-5-yl)-5,9-di-oxo-4,17-dioxa-bicyclo[14.1.0]heptadec-7-yloxycarbonyloxymethyl]-4-nitro-phenoxy}-tetrahydro-pyran-2-carboxylic acid methyl ester are isolated.

$^1$H-NMR (CDCl$_3$): δ=1.03 (3H), 1.08-1.84 (6H), 1.12 (3H), 1.17 (3H), 1.32 (3H), 2.07 (3H), 2.08 (6H), 2.08-2.17 (3H), 2.28-2.57 (4H), 2.71 (1H), 2.79 (3H), 2.84 (1H), 3.43 (1H), 3.71 (1H), 3.73 (3H), 4.27 (1H), 4.74 (1H), 4.81 (1H), 5.01 (1H), 5.05 (1H), 5.24-5.43 (5H), 5.73 (1H), 6.04 (1H), 7.11 (1H), 7.28 (1H), 7.80 (1H), 7.86 (1H), 8.03 (1H), 8.15 (1H) ppm.

Example ELE5

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenoxy}-3, 4,5-trihydroxy-tetrahydro-pyran-2-carboxylic acid

Example ELE5a (2S,3S,4S,5R,6S)-6-{4-[(4S,7R,8S,9S,13Z,16S)-7-Allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-nitro-phenoxy}-3,4,5-tris-(tert-butyl-dimethyl-silanyloxy)-tetrahydro-pyran-2-carboxylic acid allyl ester Analogously to Example ELE1c, 230 mg (312 μmol) of the compound that is presented according to Example ELE1b is reacted with 1.32 g of the compound that is presented according to Example LE4, and after working-up and purification, 132 mg (95 μmol, 30%) of the title compound is isolated.

Example ELE5

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-nitro-phenoxy}-3, 4,5-trihydroxy-tetrahydro-pyran-2-carboxylic acid allyl ester The solution of 315 mg (226 μmol) of the compound, presented according to Example ELE5a, in a mixture that consists of 6.4 ml each of tetrahydrofuran and acetonitrile is mixed with 3.2 ml of hexafluorosilicic acid, 3.2 ml of HF-pyridine complex, and it is stirred for 16 hours at 23° C. It is poured into saturated ammonium bicarbonate solution and extracted several times with ethyl acetate. The combined organic extracts are washed with saturated sodium chloride solution, dried on sodium sulfate, and the residue that is obtained after filtration and removal of the solvent is purified by chromatography on fine silica gel. 116 mg (124 μmol, 55%) of the title compound is isolated.

$^1$H-NMR (CDCl$_3$): δ=1.02 (3H), 1.13 (3H), 1.16 (3H), 1.31-2.75 (19H), 2.78 (3H), 2.91 (1H), 3.40 (1H), 3.71 (1H), 3.79 (2H), 3.94 (1H), 4.08 (1H), 4.60 (1H), 4.72 (2H), 4.75 (1H), 4.95-5.09 (3H), 5.16 (1H), 5.28 (1H), 5.36 (1H), 5.55 (1H), 5.71 (1H), 5.86-6.00 (2H), 7.21 (2H), 7.34 (1H), 7.54 (1H), 7.74 (1H), 7.91 (1H) ppm.

Example ELE6

(2S,3S,4S,5R,6S)-6-{4-[(1S,3S,7S,10R,11S,12S, 16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxyrnethyl]-2-nitro-phenoxy}-3,4,5-trihydroxy-tetrahydro-pyran-2-carboxylic acid allyl ester Analogously to Example ELE2, 50 mg (53 μmol) of the compound that is presented according to Example ELE5 is reacted, and after working-up and purification, 26 mg (27 μmol, 51%) of the title compound as well as 7 mg (7 μmol, 14%) of (2S,3S,4S,5R,6S)-6-{4-[(1R,3S,7S,10R,11S,12S, 16S)-10-allyl-11-hydroxy-8,8,12,16-tetramethyl-3-(2-methyl-benzothiazol-5-yl)-5,9-dioxo-4,17-dioxa-bicyclo [14.1.0]-heptadec-7-yloxycarbonyloxymethyl]-2-nitro-phenoxy}-3,4,5-trihydroxy-tetrahydro-pyran-2-carboxylic acid allyl ester are isolated.

Example ELE7

(2S,3S,4S,5R,6S)-6-{4-[(1S,3S,7S,10R,11S,12S, 16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxyrnethyl]-2-nitro-phenoxy}-3,4,5-trihydroxy-tetrahydro-pyran-2-carboxylic acid The solution of 26 mg (27 μmol) of the compound, presented according to Example ELE6, in 0.7 ml of dichloromethane is mixed with 1 mg of tetrakis-triphenylphosphine-palladium (0), 4 μl of pyrrolidine, and it is stirred for 1 hour at 23° C. It is mixed with 300 μl of a 5% aqueous citric acid, extracted with dichloromethane, washed with water and saturated sodium chloride solution and dried on sodium sulfate. The residue that is obtained after filtration and removal of the solvent is purified by chromatography, and 13.4 mg (15 µmol, 54%) of the title compound is isolated.

$^1$H-NMR (CD$_3$OD): δ=1.04 (3H), 1.11 (3H), 1.25 (3H), 1.33 (3H), 1.40-1.83 (7H), 2.12 (2H), 2.37 (1H), 2.58-2.85 (3H), 2.83 (3H), 2.99 (1H), 3.44-3.60 (5H), 3.77 (2H), 4.64 (1H), ~4.95-5.07 (4H), 5.46 (1H), 5.77 (1H), 6.06 (1H), 7.33-7.45 (3H), 7.63 (1H), 7.86 (1H), 7.94 (1H) ppm.

Example ELE8

(2S,3S,4S,5R,6S)-6-{4-[(4S,7R,8S,9S,13Z,16S)-7-Allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenoxy}-3,4,5-trihydroxy-tetrahydro-pyran-2-carboxylic acid allyl ester Example ELE8a (4S,7R,8S,9S,13Z,16S)-7-Allyl-4-(tert-butyl-dimethyl-silanyloxy)-8-hydroxy-5,5,9,13-tetramethyl-16-(2-methyl-benzothiazol-5-yl)-oxacyclohexadec-13-ene-2,6-dione The solution of 5.3 g (7.01 mmol) of (4S,7R,8S,9S,13Z,16S)-7-allyl-4,8-bis(tert-butyl-dimethyl-silanyloxy)-5,5,9,13-tetramethyl-16-(2-methyl-benzothiazol-5-yl)-oxacyclohexadec-13-ene-2,6-dione, which was produced analogously to the process that is described in WO 00/66589, in a mixture that consists of 85 ml of tetrahydrofuran and 85 ml of acetonitrile is mixed with 31.7 ml of hexafluorosilicic acid, cooled to 0° C., 8.1 ml of trifluoroacetic acid is added in drops, and it is stirred for 20 hours at 0° C. It is poured into water, neutralized by adding a saturated sodium bicarbonate solution and extracted several times with ethyl acetate. The combined organic extracts are washed with saturated sodium chloride solution, dried on sodium sulfate, and the residue that is obtained after filtration and removal of the solvent is purified by chromatography on fine silica gel. 2.82 g (4.39 mmol, 63%) of the title compound is isolated as a colorless solid.

$^1$H-NMR (CDCl$_3$): δ=−0.09 (3H), 0.08 (3H), 0.84 (9H), 1.08 (3H), 1.10 (3H), 1.12 (3H), 1.21-1.86 (5H), 1.70 (3H), 2.15 (1H), 2.29-2.97 (8H), 2.84 (3H), 3.14 (1H), 3.96 (1H), 4.03 (1H), 4.97-5.06 (2H), 5.23 (1H), 5.61 (1H), 5.77 (1H), 7.35 (1H), 7.79 (1H), 7.93 (1H) ppm.

Example ELE8b (4S,7R,8S,9S,13Z,16S)-Chloroformic acid-7-allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yl ester Analogously to Example ELE1b, 1.0 g (1.56 mmol) of the compound that is presented according to Example ELE8a is reacted, and 1.05 g (1.49 mmol, 96%) of the title compound is isolated.

Example ELE8c (2S,3S,4S,5R,6S)-6-{4-[(4S,7R,8S,9S,13Z,16S)-7-Allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-2-nitro-phenoxy}-3,4,5-tris-(tert-butyl-dimethyl-silanyloxy)-tetrahydro-pyran-2-carboxylic acid allyl ester Analogously to Example ELE1c, 250 mg (350 µmol) of the compound that is presented according to Example ELE8b is reacted with 1.63 g of the compound that is presented according to Example LE4, and after working-up and purification, 260 mg (186 µmol, 53%) of the title compound is isolated.

Example ELE8

(2S,3S,4S,5R,6S)-6-{4-[(4S,7R,8S,9S,13Z,16S)-7-Allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-nitro-phenoxy}-3,4,5-trihydroxy-tetrahydro-pyran-2-carboxylic acid allyl ester Analogously to Example ELE5, 321 mg (230 µmol) of the compound that is presented according to Example ELE8c is reacted, and after working-up and purification, 77 mg (82 µmol, 36%) of the title compound is isolated.

$^1$H-NMR (CDCl$_3$): δ=1.02 (3H), 1.06 (3H), 1.24 (3H), 1.38-2.00 (7H), 1.70 (3H), 2.27-2.45 (4H), 2.50 (2H), 2.85 (4H), 2.96-3.49 (3H), 3.54 (1H), 3.77 (2H), 3.94 (1H), 4.05 (2H), 4.73 (2H), 4.89-5.01 (3H), 5.09-5.25 (4H), 5.29 (1H), 5.38 (1H), 5.70 (1H), 5.84 (1H), 5.93 (1H), 7.34 (1H), 7.40 (1H), 7.60 (1H), 7.79 (1H), 7.92 (1H), 7.98 (1H) ppm.

Example ELE9

(2S,3S,4S,5R,6S)-6-{4-[(1S,3S,7S,10R,11S,12S,16R)-10-Allyl-7-hydroxy-8,8,12,16-tetramethyl-3-(2-methyl-benzothiazol-5-yl)-5,9-dioxo-4,17-dioxa-bicyclo[14.1.0]-heptadec-11-yloxycarbonyloxymethyl]-2-nitro-phenoxy}-3,4,5-trihydroxy-tetrahydro-pyran-2-carboxylic acid allyl ester Analogously to Example ELE2, 82 mg (87 µmol) of the compound that is presented according to Example ELE8 is reacted, and after working-up and purification, 57 mg (60 µmol, 69%) of the title compound as well as 8 mg (8.4 µmol, 10%) of (2S,3S,4S,5R,6S)-6-{4-[(RS,3S,7S,10R,11S,12S,16S)-10-allyl-7-hydroxy-8,8,12,16-tetramethyl-3-(2-methyl-benzothiazol-5-yl)-5,9-dioxo-4,17-dioxa-bicyclo[14.1.0]heptadec-11-yloxycarbonyloxymethyl]-2-nitro-phenoxy}-3,4,5-trihydroxy-tetrahydro-pyran-2-carboxylic acid allyl ester are isolated.

Example ELE10

(2S,3S,4S,5R,6S)-6-{4-[(1S,3S,7S,10R,11S,12S, 16R)-10-Allyl-7-hydroxy-8,8,12,16-tetramethyl-3-(2-methyl-benzothiazol-5-yl)-5,9-dioxo-4,17-dioxa-bicyclo[14.1.0]-heptadec-11-yloxycarbonyloxymethyl]-2-nitro-phenoxy}-3,4,5-trihydroxy-tetrahydro-pyran-2-carboxylic acid The solution of 57 mg (60 µmol) of the compound, presented according to Example ELE9, in 1.8 ml of dichloromethane is mixed with 14.8 µl of phenylsilane, in portions with a total of 2.9 mg of tetrakis-triphenylphosphine palladium (0), and it is stirred for 19 hours at 23° C. It is concentrated by evaporation, the residue that is obtained is purified by chromatography, and 27 mg (30 µmol, 49%) of the title compound is isolated.

$^1$H-NMR (DMSO-d6): δ=0.91 (3H), 0.93 (3H), 1.07-2.75 (15H), 1.17 (3H), 1.23 (3H), 2.80 (3H), 2.93 (1H), 3.08-3.48 (4H), 3.61 (1H), 4.06 (1H), 4.87 (1H), 4.92 (1H), 4.99 (2H), 5.06 (1H), 5.14-5.25 (4H), 5.67 (1H), 5.96 (1H), 7.44 (1H), 7.48 (1H), 7.65 (1H), 7.90 (1H), 7.99 (2H) ppm.

Example ELE11

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenoxy}-3,4,5-trihydroxy-tetrahydro-pyran-2-carboxylic acid allyl ester

Example ELE11a (2S,3S,4S,5R,6S)-6-{4-[(4S,7R,8S,9S,13Z,16S)-7-Allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-phenoxy}-3,4,5-tris-(tert-butyl-dimethyl-silanyloxy)-tetrahydro-pyran-2-carboxylic acid allyl ester The solution of 1.7 g (2.41 mmol) of the compound, presented according to Example ELE1b, in 51 ml of toluene, is mixed with 10.7 g of the compound that is presented according to Example LE5, 210 mg of sodium bicarbonate, and it is stirred for 16 hours at 23° C. It is filtered, concentrated by evaporation, and the residue is purified by chromatography on fine silica gel. 1.95 g (1.44 mmol, 60%) of the title compound is isolated.

Example ELE11

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-phenoxy}-3,4,5-trihydroxy-tetrahydro-pyran-2-carboxylic acid allyl ester The solution of 1.95 g (1.44 mmol) of the compound, presented according to Example ELE11a, in 87 ml of tetrahydrofuran is mixed in portions with a total of 7 ml of HF-pyridine complex over several hours, and it is, stirred for a total of 24 hours at 23° C. It is poured into saturated ammonium bicarbonate solution and extracted several times with ethyl acetate. The combined organic extracts are washed with saturated sodium chloride solution, dried on sodium sulfate, and the residue that is obtained after filtration and removal of the solvent is purified by chromatography on fine silica gel. 766 mg (857 µmol, 59%) of the title compound is isolated.

$^1$H-NMR (CDCl$_3$): δ=1.01 (3H), 1.13 (6H), 1.18-1.89 (6H), 1.69 (3H), 2.18-2.54 (5H), 2.57 (1H), 2.66 (1H), 2.79 (3H), 2.88 (1H), 3.23 (1H), 3.36 (1H), 3.41 (1H), 3.66-3.95 (5H), 4.01 (1H), 4.56 (1H), 4.64-4.78 (3H), 4.93 (1H), 5.01 (1H), 5.05 (1H), 5.14 (1H), 5.26 (1H), 5.34 (1H), 5.57 (1H), 5.72 (1H), 5.84-5.97 (2H), 6.81 (2H), 6.94 (2H), 7.34 (1H), 7.74 (1H), 7.86 (1H) ppm.

Example ELE12

(2S,3S,4S,5R,6S)-6-{4-[(1S,3S,7S,10R,11S,12S, 16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxymethyl]-phenoxy}-3,4,5-trihydroxy-tetrahydro-pyran-2-carboxylic acid allyl ester Analogously to Example ELE2, 766 mg (857 µmol) of the compound that is presented according to Example ELE11 is reacted, and after working-up and purification, 616 mg (677 µmol, 79%) of the title compound is isolated.

$^1$H-NMR (CDCl$_3$): δ=1.03 (3H), 1.11 (3H), 1.19 (3H), 1.31 (3H), 1.23-1.83 (6H), 1.96 (2H), 2.30-2.58 (4H), 2.68 (1H), 2.79 (1H), 2.81 (3H), 3.39-3.93 (10H), 4.61-4.79 (5H), 5.02 (1H), 5.06 (1H), 5.26 (1H), 5.34 (1H), 5.43 (1H), 5.72 (1H), 5.88 (1H), 5.97 (1H), 6.84 (2H), 7.05 (2H), 7.26 (1H), 7.76 (1H), 7.84 (1H) ppm.

Example ELE13

(2S,3S,4S,5R,6S)-6-{4-[(1S,3S,7S,10R,11S,12S, 16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxymethyl]-phenoxy}-3,4,5-trihydroxy-tetrahydro-pyran-2-carboxylic acid Analogously to Example ELE10, 320 mg (352 µmol) of the compound that is presented according to Example ELE12 is reacted, and after working-up and purification, 165 mg (190 µmol, 54%) of the title compound is isolated.

$^1$H-NMR (d6-DMSO): δ=0.90 (3H), 0.98 (3H), 1.13 (3H), 1.23 (3H), 1.06-1.58 (5H), 1.67 (1H), 2.02 (1H), 2.09-2.31 (2H), 2.41-2.78 (4H), 2.80 (3H), 2.90 (1H), 3.06-3.40 (6H), 3.60 (1H), 4.66-4.80 (3H), 4.88-5.03 (4H), 5.18 (1H), 5.27 (1H), 5.69 (1H), 5.99 (1H), 6.95 (2H), 7.15 (2H), 7.34 (1H), 7.37 (1H), 7.88 (1H), 8.02 (1H) ppm.

Example ELE14

(2S,3S,4S,5R,6S)-6-{4-[(4S,7R,8S,9S,13Z,16S)-7-Allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenoxy}-3,4,5-trihydroxy-tetrahydro-pyran-2-carboxylic acid allyl ester

Example ELE14a (2S,3S,4S,5R,6S)-6-{4-[(4S,7R,8S,9S,13Z,16S)-7-Allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-phenoxy}-3,4,5-tris-(tert-butyl-dimethyl-silanyloxy)-tetrahydro-pyran-2-carboxylic acid allyl ester Analogously to Example ELE1a, 1.95 g (2.77 mmol) of the compound that is presented according to Example ELE8b is reacted with the compound that is presented according to Example LE5, and after working-up and purification, 2.79 g (2.06 mmol, 75%) of the title compound is isolated.

Example ELE14

(2S,3S,4S,5R,6S)-6-{4-[(4S,7R,8S,9S,13Z,16S)-7-Allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-phenoxy}-3,4,5-trihydroxy-tetrahydro-pyran-2-carboxylic acid allyl ester Analogously to Example ELE11, 2.78 g (2.06 mmol) of the compound that is presented according to Example ELE14a is reacted, and after working-up and purification, 1.00 g (1.12 mmol, 54%) of the title compound is isolated.

$^1$H-NMR (CDCl$_3$): δ=1.00 (3H), 1.06 (3H), 1.13 (1H), 1.21 (3H), 1.48-1.96 (5H), 1.70 (3H), 2.25-2.54 (6H), 2.83 (3H), 2.87 (1H), 3.01 (1H), 3.10 (1H), 3.35 (1H), 3.46 (1H), 3.53 (1H), 3.74 (2H), 3.90 (1H), 3.98 (2H), 4.71 (2H), 4.86-5.00 (3H), 5.06-5.23 (4H), 5.27 (1H), 5.35 (1H), 5.69 (1H), 5.82 (1H), 5.91 (1H), 7.05 (2H), 7.23 (3H), 7.79 (1H), 7.95 (1H) ppm.

Example ELE15

(2S,3S,4S,5R,6S)-6-{4-[(1S,3S,7S,10R,11S,12S,16R)-10-Allyl-7-hydroxy-8,8,12,16-tetramethyl-3-(2-methyl-benzothiazol-5-yl)-5,9-dioxo-4,17-dioxa-bicyclo[14.1.0]-heptadec-11-yloxycarbonyloxymethyl]-phenoxy}-3,4,5-trihydroxy-tetrahydro-pyran-2-carboxylic acid allyl ester Analogously to Example ELE2, 1.30 g (1.45 mmol) of the compound that is presented according to Example ELE14 is reacted, and after working-up and purification, 1.15 g (1.26 mmol, 87%) of the title compound is isolated.

$^1$H-NMR (d6-DMSO): δ=0.92 (3H), 0.93 (3H), 1.17 (3H), 1.19 (3H), 1.23-1.68 (7H), 2.04 (1H), 2.17 (1H), 2.28 (2H), 2.38 (1H), 2.62 (1H), 2.80 (3H), 2.93 (1H), 3.25-3.47 (3H), 3.60 (1H), 4.06 (1H), 4.10 (1H), 4.61 (2H), 4.87 (1H), 4.91 (1H), 4.99 (1H), 5.08 (2H), 5.11-5.22 (3H), 5.28 (1H), 5.32 (1H), 5.45 (1H), 5.51 (1H), 5.67 (1H), 5.88 (1H), 5.97 (1H), 7.03 (2H), 7.33 (2H), 7.47 (1H), 7.99 (2H) ppm.

Example ELE16

(2S,3S,4S,5R,6S)-6-{4-[(1 S,3S,7S,10R,11S,12S,16R)-10-Allyl-7-hydroxy-8,8,12,16-tetramethyl-3-(2-methyl-benzothiazol-5-yl)-5,9-dioxo-4,17-dioxa-bicyclo[14.1.0]-heptadec-11-yloxycarbonyloxymethyl]-phenoxy}-3,4,5-trihydroxy-tetrahydro-pyran-2-carboxylic acid Analogously to Example ELE10, 354 mg (389 µmol) of the compound that is presented according to Example ELE15 is reacted, and after working-up and purification, 187 mg (215 µmol, 55%) of the title compound is isolated.

$^1$H-NMR (d6-DMSO): δ=0.92 (3H), 0.93 (3H), 1.18 (3H), 1.20 (3H), 1.00-1.68 (5H), 2.04 (1H), 2.16 (1H), 2.28 (2H), 2.38 (2H), 2.61 (1H), 2.80 (3H), 2.94 (1H), 3.07-3.40 (6H), 3.61 (1H), 4.07 (1H), 4.81 (1H), 4.88 (1H), 4.91-5.03 (3H), 5.09 (2H), 5.19 (1H), 5.21 (1H), 5.67 (1H), 5.96 (1H), 7.03 (2H), 7.32 (3H), 7.48 (1H), 7.99 (2H) ppm.

Example ELE17

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-chloro-phenoxy}-3,4,5-trihydroxy-tetrahydro-pyran-2-carboxylic acid allyl ester

Example ELE17a (2S,3S,4S,5R,6S)-6-{4-[(4S,7R,8S,9S,13Z,16S)-7-Allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-chloro-phenoxy}-3,5-bis-triisopropylsilanyloxy)-4-hydroxy-tetrahydro-pyran-2-carboxylic acid allyl ester The solution of 1.41 g (2.00 mmol) of the compound, presented according to Example ELE1b, in a mixture that consists of 40 ml of dimethylformamide and 16 ml of trichloromethane is mixed with 7.74 g of the compound that is presented according to Example LE6, 1.0 g of copper(I) chloride, and the suspension is stirred for 16 hours at 23° C. It is filtered, concentrated by evaporation, and the residue is purified by chromatography on fine silica gel. 770 mg (568 µmol, 28%) of the title compound is isolated.

Example ELE17

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-chloro-phenoxy}-3,4,5-trihydroxy-tetrahydro-pyran-2-carboxylic acid allyl ester Analogously to Example ELE11, 1.54 g (1.14 mmol) of the compound that is presented according to Example ELE17a is reacted, and after working-up and purification, 612 mg (659 µmol, 58%) of the title compound is isolated.

$^1$H-NMR (CDCl$_3$): δ=1.02 (3H), 1.14 (3H), 1.16 (3H), 1.70 (3H), 1.20-1.90 (5H), 2.18-2.59 (6H), 2.69 (1H), 2.77 (3H), 2.92 (1H), 3.14 (1H), 3.32 (1H), 3.37-3.53 (3H), 3.64-4.02 (5H), 4.54 (1H), 4.66-4.75 (3H), 4.86 (1H), 5.01 (1H), 5.06 (1H), 5.16 (1H), 5.28 (1H), 5.37 (1H), 5.56 (1H), 5.72 (1H), 5.90 (1H), 5.96 (1H), 6.88 (1H), 7.03 (1H), 7.08 (1H), 7.33 (1H), 7.74 (1H), 7.91 (1H) ppm.

Example ELE18

(2S,3S,4S,5R,6S)-6-{4-[(1S,3S,7S,10R,11S,12S,16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxymethyl]-2-chloro-phenoxy}-3,4,5-trihydroxy-tetrahydro-pyran-2-carboxylic acid allyl ester Analogously to Example ELE2, 610 mg (657 µmol) of the compound that is presented according to Example ELE17 is reacted, and after working-up and purification, 517 g (547 µmol, 83%) of the title compound is isolated.

$^1$H-NMR (CDCl$_3$): δ=1.03 (3H), 1.12 (3H), 1.18 (3H), 1.32 (3H), 1.07-1.83 (8H), 2.01-2.17 (2H), 2.29-2.59 (4H), 2.72 (1H), 2.80 (3H), 2.83 (1H), 3.45 (1H), 3.71 (2H), 3.81

(1H), 3.93 (1H), 3.95 (1H), 4.56 (1H), 4.63-4.75 (3H), 4.80 (1H), 5.02 (1H), 5.06 (1H), 5.27 (1H), 5.36 (1H), 5.46 (1H), 5.71 (1H), 5.92 (1H), 6.03 (1H), 6.94 (1H), 7.05 (1H), 7.10 (1H), 7.28 (1H), 7.76 (1H), 7.88 (1H) ppm.

Example ELE19

(2S,3S,4S,5R,6S)-6-{4-[(1S,3S,7S,10R,11S,12S, 16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxymethyl]-2-chloro-phenoxy}-3,4,5-trihydroxy-tetrahydro-pyran-2-carboxylic acid Analogously to Example ELE10, 310 mg (328 µmol) of the compound that is presented according to Example ELE18 is reacted, and after working-up and purification, 160 mg (177 µmol, 54%) of the title compound is isolated.

$^1$H-NMR (d6-DMSO): δ=0.92 (3H), 0.98 (3H), 1.14 (3H), 1.22 (3H), 1.07-1.72 (7H), 2.02 (1H), 2.12-2.50 (4H), 2.55 (1H), 2.66 (1H), 2.73 (1H), 2.78 (3H), 2.92 (1H), 3.12 (1H), 3.24 (1H), 3.31 (3H), 3.38 (1H), 3.59 (1H), 4.70 (1H), 4.76 (1H), 4.88-5.02 (4H), 5.18 (1H), 5.28 (1H), 5.70 (1H), 6.00 (1H), 7.15 (2H), 7.25 (1H), 7.37 (1H), 7.88 (1H), 8.02 (1H)

Example ELE20

(2S,3S,4S,5R,6S)-6-{4-[(4S,7R,8S,9S,13Z,16S)-7-Allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-chloro-phenoxy}-3,4,5-trihydroxy-tetrahydro-pyran-2-carboxylic acid allyl ester

Example ELE20a (2S,3S,4S,5R,6S)-6-{4-[(4S,7R,8S,9S,13Z,16S)-7-Allyl-4-(tert-butyl-dimethyl-silanyloxy)-5,5,9,13-tetramethyl-16-(2-methyl-benzothiazol-5-yl)-2,6-dioxo-oxacyclohexadec-13-en-8-yloxycarbonyloxymethyl]-2-chloro-phenoxy}-4-hydroxy-3,5-bis-triisopropylsilanyloxy-tetrahydro-pyran-2-carboxylic acid allyl ester Analogously to Example ELE17a, 2.13 g (3.02 mmol) of the compound that is presented according to Example ELE8b is reacted with the compound that is presented according to Example LE6, and after working-up and purification, 1.71 g (1.26 mmol, 42%) of the title compound is isolated.

Example ELE20

(2S,3S,4S,5R,6S)-6-{4-[(4S,7R,8S,9S,13Z,16S)-7-Allyl-4-hydroxy-5,5,9,13-tetramethyl-16-(2-methyl-benzothiazol-5-yl)-2,6-dioxo-oxacyclohexadec-13-en-8-yloxycarbonyloxymethyl]-2-chloro-phenoxy}-3,4,5-trihydroxy-tetrahydro-pyran-2-carboxylic acid allyl ester Analogously to Example ELE11, 930 mg (686 µmol) of the compound that is presented according to Example ELE20a is reacted, and after working-up and purification, 460 mg (495 µmol, 72%) of the title compound is isolated.

$^1$H-NMR (CDCl$_3$): δ=1.02 (3H), 1.06 (3H), 1.14 (1H), 1.22 (3H), 1.51-1.95 (6H), 1.70 (3H), 2.28-2.43 (3H), 2.50 (2H), 2.84 (3H), 2.88 (1H), 2.98 (1H), 3.10 (1H), 3.23 (1H), 3.39 (1H), 3.53 (1H), 3.73 (1H), 3.82 (1H), 3.88-4.04 (3H), 4.72 (2H), 4.85 (1H), 4.92 (1H), 4.98 (1H), 5.10 (2H), 5.15 (1H), 5.21 (1H), 5.28 (1H), 5.36 (1H), 5.70 (1H), 5.82 (1H), 5.93 (1H), 7.20-7.28 (2H), 7.33 (1H), 7.44 (1H), 7.79 (1H), 7.95 (1H) ppm.

Example ELE21

(2S,3S,4S,5R,6S)-6-{4-[(1S,3S,7S,10R,11S,12S, 16R)-10-Allyl-7-hydroxy-8,8,12,16-tetramethyl-3-(2-methyl-benzothiazol-5-yl)-5,9-dioxo-4,17-dioxa-bicyclo[14.1.0]-heptadec-11-yloxycarbonyloxymethyl]-2-chloro-phenoxy}-3,4,5-trihydroxy-tetrahydro-pyran-2-carboxylic acid allyl ester Analogously to Example ELE2, 610 mg (657 µmol) of the compound that is presented according to Example ELE20 is reacted, and after working-up and purification, 601 mg (636 µmol, 97%) of the title compound is isolated.

$^1$H-NMR (CDCl$_3$): δ=0.96 (3H), 1.03 (3H), 1.07-1.82 (8H), 1.23 (3H), 1.31 (3H), 2.15 (2H), 2.34 (2H), 2.52 (1H), 2.61 (1H), 2.71 (1H), 2.84 (3H), 3.04 (1H), 3.21 (1H), 3.45 (1H), 3.66-4.15 (6H), 4.30 (1H), 4.71 (2H), 4.85 (1H), 4.91 (1H), 4.96 (1H), 5.08 (1H), 5.21 (1H), 5.28 (1H), 5.35 (1H), 5.72 (1H), 5.92 (1H), 6.24 (1H), 7.23 (2H), 7.36 (1H), 7.42 (1H), 7.83 (1H), 8.00 (1H) ppm.

Example ELE22

(2S,3S,4S,5R,6S)-6-{4-[(1S,3S,7S,10R,11S,12S, 16R)-10-Allyl-7-hydroxy-8,8,12,16-tetramethyl-3-(2-methyl-benzothiazol-5-yl)-5,9-dioxo-4,17-dioxa-bicyclo[14.1.0]-heptadec-11-yloxycarbonyloxymethyl]-2-chloro-phenoxy}-3,4,5-trihydroxy-tetrahydro-pyran-2-carboxylic acid Analogously to Example ELE10, 302 mg (320 µmol) of the compound that is presented according to Example ELE21 is reacted, and after working-up and purification, 178 mg (197 µmol, 62%) of the title compound is isolated.

$^1$H-NMR (d6-DMSO): δ=0.93 (6H), 1.06-1.70 (6H), 1.18 (3H), 1.20 (3H), 2.05 (2H), 2.17 (1H), 2.21-2.47 (4H), 2.61 (1H), 2.80 (3H), 2.93 (1H), 3.11 (1H), 3.26 (2H), 3.32 (1H), 3.42 (1H), 3.62 (1H), 4.08 (1H), 4.85-5.04 (5H), 5.09 (2H), 5.20 (2H), 5.67 (1H), 5.96 (1H), 7.19-7.36 (3H), 7.45 (1H), 7.48 (1H), 7.99 (2H) ppm.

Example ELE23

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-methoxy-phenoxy}-3,4,5-trihydroxy-tetrahydro-pyran-2-carboxylic acid allyl ester

Example ELE23a (2S,3S,4S,5R,6S)-6-{4-[(4S,7R,8S,9S,13Z,16S)-7-Allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-methoxy-phenoxy}-3,4,5-tris-(tert-butyl-dimethyl-silanyloxy)-tetrahydro-pyran-2-carboxylic acid allyl ester Analogously to Example ELE1c, 1.15 g (1.63 mmol) of the compound that is presented according to Example ELE1b is reacted with the compound that is presented according to Example LE7, and after working-up and purification, 1.44 g (1.04 mmol, 64%) of the title compound is isolated.

Example ELE23

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-methoxy-phenoxy}-3,4,5-trihydroxy-tetrahydro-pyran-2-carboxylic acid allyl ester Analogously to Example ELE11, 1.44 g (1.04 mmol) of the compound that is presented according to Example ELE23a is reacted, and after working-up and purification, 386 mg (418 µmol, 40%) of the title compound is isolated.

$^1$H-NMR (CDCl$_3$): δ=1.01 (3H), 1.13 (3H), 1.15 (3H), 1.31-1.90 (5H), 1.70 (3H), 2.25 (1H), 2.30-2.55 (4H), 2.58 (1H), 2.68 (1H), 2.74 (3H), 2.94 (1H), 3.40 (1H), 3.46-3.97 (8H), 3.79 (3H), 4.04 (1H), 4.56 (1H), 4.68-4.78 (4H), 5.00 (1H), 5.04 (1H), 5.16 (1H), 5.27 (1H), 5.35 (1H), 5.55 (1H), 5.71 (1H), 5.92 (2H), 6.57 (1H), 6.60 (1H), 7.06 (1H), 7.34 (1H), 7.73 (1H), 7.92 (1H) ppm.

Example ELE24

(2S,3S,4S,5R,6S)-6-{4-[(1S,3S,7S,10R,11S,12S,16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxymethyl]-2-methoxy-phenoxy}-3,4,5-trihydroxy-tetrahydro-pyran-2-carboxylic acid allyl ester Analogously to Example ELE2, 384 mg (416 µmol) of the compound that is presented according to Example ELE23 is reacted, and after working-up and purification, 278 mg (296 µmol, 71%) of the title compound is isolated.

$^1$H-NMR (CDCl$_3$): δ=1.04 (3H), 1.11 (3H), 1.18 (3H), 1.32 (3H), 1.20-2.59 (13H), 2.70 (1H), 2.79 (4H), 3.17 (1H), 3.32 (1H), 3.44 (1H), 3.58-3.92 (6H), 3.82 (3H), 4.55-4.80 (5H), 5.01 (1H), 5.05 (1H), 5.28 (1H), 5.37 (1H), 5.44 (1H), 5.72 (1H), 5.91 (1H), 5.99 (1H), 6.69 (2H), 7.02 (1H), 7.26 (1H), 7.76 (1H), 7.87 (1H) ppm.

Example ELE25

(2S,3S,4S,5R,6S)-6-{4-[(1S,3S,7S,10R,11S,12S,16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxymethyl]-2-methoxy-phenoxy}-3,4,5-trihydroxy-tetrahydro-pyran-2-carboxylic acid Analogously to Example ELE10, 100 mg (106 µmol) of the compound that is presented according to Example ELE24 is reacted, and after working-up and purification, 64 mg (71 µmol, 67%) of the title compound is isolated.

$^1$H-NMR (d6-DMSO): δ=0.91 (3H), 0.98 (3H), 1.15 (3H), 1.23 (3H), 1.07-2.76 (11H), 2.79 (3H), 2.90 (1H), 3.05-3.42 (8H), 3.59 (1H), 3.72 (3H), 4.66-5.01 (7H), 5.09 (1H), 5.27 (1H), 5.71 (1H), 5.98 (1H), 6.75 (1H), 6.85 (1H), 7.00 (1H), 7.36 (2H), 7.88 (1H), 8.02 (1H) ppm.

Example ELE26

(2S,3S,4S,5R,6S)-6-{4-[(4S,7R,8S,9S,13Z,16S)-7-Allyl-8-hydroxy-5,5,9,13-tetramethyl-16-(2-methyl-benzothiazol-5-yl)-2,6-dioxo-oxacyclohexadec-13-en-4-yloxycarbonyloxymethyl]-2-fluoro-phenoxy}-3,4,5-trihydroxy-tetrahydro-pyran-2-carboxylic acid allyl ester Example ELE26a (2S,3S,4S,5R,6S)-6-{4-[(4S,7R,8S,9S,13Z,16S)-7-Allyl-8-(tert-butyl-dimethyl-silanyloxy)-5,5,9,13-tetramethyl-16-(2-methyl-benzothiazol-5-yl)-2,6-dioxo-oxacyclohexadec-13-en-4-yloxycarbonyloxymethyl]-2-methoxy-phenoxy}-3,4,5-tris-(tert-butyl-dimethyl-silanyloxy)-tetrahydro-pyran-2-carboxylic acid allyl ester Analogously to Example ELE1c, 2.0 g (2.84 mmol) of the compound that is presented according to Example ELE1b is reacted with the compound that is presented according to Example LE8, and after working-up and purification, 2.06 g (1.50 mmol, 53%) of the title compound is isolated.

Example ELE26

(2S,3S,4S,5R,6S)-6-{4-[(4S,7R,8S,9S,13Z,16S)-7-Allyl-8-hydroxy-5,5,913-tetramethyl-16-(2-methyl-benzothiazol-5-yl)-2,6-dioxo-oxacyclohexadec-13-en-4-yloxycarbonyloxymethyl]-2-fluoro-phenoxy}-3,4,5-trihydroxy-tetrahydro-pyran-2-carboxylic acid allyl ester Analogously to Example ELE11, 2.06 g (1.50 mmol) of the compound that is presented according to Example ELE26a is reacted, and after working-up and purification, 1.01 g (1.11 mmol, 74%) of the title compound is isolated.

$^1$H-NMR (CDCl$_3$): δ=1.02 (3H), 1.14 (6H), 1.20-2.61 (11H), 1.70 (3H), 2.68 (1H), 2.78 (3H), 2.91 (1H), 3.18-4.01 (10H), 4.56 (1H), 4.65-4.76 (3H), 4.90 (1H), 5.01 (1H), 5.06 (1H), 5.16 (1H), 5.27 (1H), 5.34 (1H), 5.55 (1H), 5.72 (1H), 5.89 (1H), 5.93 (1H), 6.73 (2H), 7.05 (1H), 7.33 (1H), 7.73 (1H), 7.88 (1H) ppm.

Example ELE27

(2S,3S,4S,5R,6S)-6-{4-[(1S,3S,7S,10R,11S,12S,16R)-10-Allyl-11-hydroxy-8,8,12,16-tetramethyl-3-(2-methyl-benzothiazol-5-yl)-5,9-dioxo-4,17-dioxa-bicyclo[14.1.0]-heptadec-7-yloxycarbonyloxymethyl]-2-fluoro-phenoxy}-3,4,5-trihydroxy-tetrahydro-pyran-2-carboxylic acid allyl ester Analogously to Example ELE2, 1.01 g (1.11 mmol) of the compound that is presented according to Example ELE26 is reacted, and after working-up and purification, 657 mg (708 µmol, 64%) of the title compound is isolated.

$^1$H-NMR (CDCl$_3$): δ=1.04 (3H), 1.13 (3H), 1.32 (3H), 1.31 (3H), 1.24-1.84 (7H), 1.98-2.17 (2H), 2.29-2.59 (4H), 2.71 (1H), 2.80 (3H), 2.82 (1H), 3.29 (1H), 3.38 (1H), 3.45 (1H), 3.64-3.96 (6H), 4.59 (1H), 4.65-4.73 (3H), 4.83 (1H), 5.01 (1H), 5.06 (1H), 5.26 (1H), 5.34 (1H), 5.46 (1H), 5.71 (1H), 5.91 (1H), 6.01 (1H), 6.81 (2H), 7.04 (1H), 7.28 (1H), 7.75 (1H), 7.86 (1H) ppm.

Example ELE28

(2S,3S,4S,5R,6S)-6-{4-[(1S,3S,7S,10R,11S,12S,16R)-10-Allyl-11-hydroxy-8,8,12,16-tetramethyl-3-(2-methyl-benzothiazol-5-yl)-5,9-dioxo-4,17-dioxabicyclo[14.1.0]-heptadec-7-yloxycarbonyloxymethyl]-2-fluoro-phenoxy}-3,4,5-trihydroxy-tetrahydro-pyran-2-carboxylic acid Analogously to Example ELE10, 350 mg (377 µmol) of the compound that is presented according to Example ELE27 is reacted, and after working-up and purification, 234 mg (264 µmol, 70%) of the title compound is isolated.

$^1$H-NMR (d6-DMSO): δ=0.92 (3H), 0.98 (3H), 1.14 (3H), 1.23 (3H), 1.08-1.60 (7H), 1.66 (1H), 2.02 (1H), 2.11-2.75 (5H), 2.78 (3H), 2.91 (1H), 3.01-3.41 (5H), 3.60 (1H), 4.69 (1H), 4.77 (1H), 4.86 (1H), 4.89-5.02 (4H), 5.25 (1H), 5.28 (1H), 5.71 (1H), 5.99 (1H), 6.99 (1H), 7.06 (1H), 7.19 (1H), 7.26 (1H), 7.37 (1H), 7.87 (1H), 8.02 (1H) ppm.

The entire disclosure[s] of all applications, patents and publications, cited herein and of corresponding German application No. 10256982.7, filed Dec. 5, 2002 and of Provisional U.S. Application No. 60/431,197, filed Dec. 6, 2002, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A conjugate compound of formula (I):

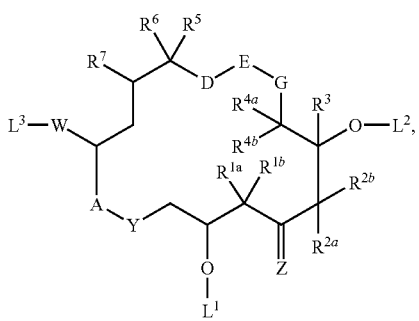

I in which
- $R^{1a}$, $R^{1b}$, independently of one another, are hydrogen, $C_1$-$C_{10}$ alkyl, aryl, aralkyl, or together a —$(CH_2)_m$— group, in which m is 2 to 5,
- $R^{2a}$ and $R^{2b}$, independently of one another, are hydrogen, $C_1$-$C_{10}$ alkyl, aryl, aralkyl, or together a —$(CH_2)_n$— group, in which n is 2 to 5, or $C_2$-$C_{10}$ alkenyl, or $C_2$-$C_{10}$ alkinyl,
- $R^3$ is hydrogen, $C_1$-$C_{10}$ alkyl, aryl or aralkyl, and
- $R^{4a}$ and $R^{4b}$, independently of one another, are hydrogen, $C_1$-$C_{10}$ alkyl, aryl, aralkyl, or together a —$(CH_2)_p$— group, in which p is 2 to 5,
- $R^5$ is hydrogen, $C_1$-$C_{10}$ alkyl, aryl, aralkyl, $CO_2H$, $CO_2$alkyl, $CH_2OH$, $CH_2O$alkyl, $CH_2O$acyl, CN, $CH_2NH_2$, $CH_2N$(alkyl, acyl)$_{1,2}$, or $CH_2$Hal,
- Hal is a halogen atom,
- $R^6$ and $R^7$, in each case, are hydrogen, or together an additional bond or together an oxygen atom, or together an NH group, or together an N-alkyl group, or together a $CH_2$ group, and
- G is an oxygen atom or $CH_2$,
- D-E is a group $H_2C$—$CH_2$, HC=CH, C≡C, CH(OH)—CH(OH), CH(OH)—$CH_2$, $CH_2$—CH(OH)

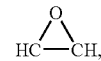

O—$CH_2$, or, if G represents a $CH_2$ group, is additionally $CH_2$—O,
- W is a group C(=X)$R^8$, or a bi- or tricyclic aromatic or heteroaromatic radical,
- $L^3$ is hydrogen, or, if a radical in W contains a hydroxyl group, forms a group O-$L^4$ with the latter, or, if a radical in W contains an amino group, optionally forms a group $NR^{25}$-$L^4$ with the latter,
- $R^{25}$ is hydrogen or $C_1$-$C_{10}$ alkyl,
- X is an oxygen atom, or two $OR^{20}$ groups, or a $C_2$-$C_{10}$ alkylenedioxy group, which is straight-chain or branched, or H/$OR^9$, or a $CR^{10}R^{11}$ group,
- $R^8$ is hydrogen, $C_1$-$C_{10}$ alkyl, aryl, aralkyl, halogen or CN, and
- $R^9$ is hydrogen or a protective group $PG^X$,
- $R^{10}$ and $R^{11}$, in each case independently of one another, are hydrogen, $C_1$-$C_{20}$ alkyl, aryl, or aralkyl, or together with a methylene carbon atom form a 5- to 7-membered carbocyclic ring,
- Z is oxygen or H/$OR^{12}$,
- $R^{12}$ is hydrogen or a protective group $PG^Z$,
- A-Y is a group O—C(=O), O—$CH_2$, $CH_2$—C(=O), $NR^{21}$—C(=O) or $NR^{21}$—$SO_2$,
- $R^{20}$ can represent $C_1$-$C_{20}$ alkyl,
- $R^{21}$ can represent a hydrogen atom or $C_1$-$C_{10}$ alkyl,
- $PG^X$, $PG^Y$, and $PG^Z$ can represent a protective group PG, and
- $L^1$, $L^2$, $L^4$, independently of one another, are hydrogen, a group C(=O)Cl, a group C(=S)Cl, a group $PG^Y$ or a linker-recognition unit of formula (III);
- with the condition that at least one substituent $L^1$, $L^2$ or $L^4$ represents a linker-recognition unit of general formula (III);

the linker-recognition unit of general formula (III) has the following structure,

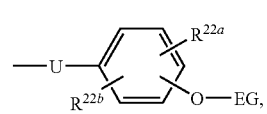

III in which
- $R^{22a}$ and $R^{22b}$, independently of one another, are hydrogen, $C_1$-$C_{20}$ alkyl, $C_1$-$C_{20}$ acyl, $C_1$-$C_{20}$ acyloxy, aryl, aralkyl, hydroxy, alkoxy, $CO_2H$, $CO_2$alkyl, halogen, CN, $NO_2$, $NH_2$, or $N_3$, U is —C(=O)NR²³—, —C(=S)NR²³—, —C(=O)NR²³—CH₂—, —C(=S)NR²³—CH₂—, —C(=O)O—, —C(=S)O—, —C(=O)O—CH₂—, or —C(=S)O—CH₂—, $R^{23}$ is hydrogen or $C_1$-$C_{10}$ alkyl, and EG is a recognition unit of general formula (IV):

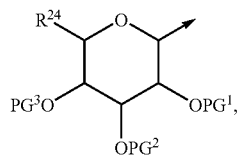

in which $R^{24}$ can represent a group CH₂OPG⁴ or a group CO₂R²⁶,

PG¹, PG², PG³, and PG⁴, independently of one another, are hydrogen or a protective group PG, $R^{26}$ is hydrogen, $C_1$-$C_{20}$ alkyl, $C_1$-$C_{20}$ alkenyl, $C_4$-$C_7$ cycloalkyl, which can contain an oxygen atom, aryl, aralkyl, tris($C_1$-$C_{20}$ alkyl)silyl, bis($C_1$-$C_{20}$ alkyl)-arylsilyl, ($C_1$-$C_{20}$ alkyl)-diarylsilyl, or tris(aralkyl)-silyl, as a uniform isomer or a mixture of different isomers and/or as a pharmaceutically acceptable salt thereof.

2. A conjugate compound according to claim 1, whereby:

A-Y represents O—C(=O) or NR²¹—C(=O),

D-E represents an H₂C—CH₂ group or an HC=CH group,

G represents a CH₂ group,

Z represents an oxygen atom, $R^{1a}$ and $R^{1b}$ in each case represent $C_1$-$C_{10}$ alkyl or together a —(CH₂)$_p$ group with p equal to 2 or 3 or 4, $R^{2a}$ and $R^{2b}$, independently of one another, represent hydrogen, $C_1$-$C_{10}$ alkyl, $C_2$-$C_{10}$ alkenyl, or $C_2$-$C_{10}$ alkinyl, $R^3$ represents hydrogen;

$R^{4a}$ and $R^{4b}$, independently of one another, represent hydrogen or $C_1$-$C_{10}$ alkyl;

$R^5$ represents hydrogen or $C_1$-$C_4$ alkyl or CH₂OH or CH₂NH₂ or CH₂N(alkyl, acyl)$_{1,2}$ or CH₂Hal, $R^6$ and $R^7$ together represent an additional bond or together an NH group or together an N-alkyl group or together a CH₂ group or together an oxygen atom, W represents a group C(=X)R⁸ or a 2-methylbenzothiazol-5-yl radical or a 2-methylbenzoxazol-5-yl radical or a quinolin-7-yl radical or a 2-aminomethylbenzothiazol-5-yl radical or a 2-hydroxymethylbenzothiazol-5-yl radical or a 2-aminomethylbenzoxazol-5-yl radical or a 2-hydroxymethylbenzoxazol-5-yl radical, X represents a CR¹⁰R¹¹ group, $R^8$ represents hydrogen or $C_1$-$C_4$ alkyl or a fluorine atom or a chlorine atom or a bromine atom, $R^{10}$/$R^{11}$ represent hydrogen/2-methylthiazol-4-yl or hydrogen/2-pyridyl or hydrogen/2-methyloxazol-4-yl or hydrogen/2-aminomethylthiazol-4-yl or hydrogen/2-aminomethyloxazol-4-yl or hydrogen/2-hydroxymethylthiazol-4-yl or hydrogen/2-hydroxymethyloxazol-4-yl.

3. A conjugate compound according to claim 1, whereby:

$R^{22a}$ and $R^{22b}$ represent $C_1$-$C_8$-alkyl, $C_1$-$C_8$-alkoxy, halogen, nitro, CN, N₃, NH₂, or CO₂—($C_1$-$C_8$-alkyl).

4. A conjugate compound according to claim 1, whereby:

$R^{26}$ represents $C_1$-$C_8$-alkyl or $C_2$-$C_8$-alkenyl.

5. A conjugate compound according to claim 1, whereby:

$R^{2a}$ represents hydrogen and $R^{2b}$ represents $C_1$-$C_7$-alkyl, $C_2$-$C_7$-alkenyl or $C_2$-$C_7$-alkinyl; or $R^{2b}$ represents hydrogen and $R^{2a}$ represents $C_1$-$C_7$-alkyl, $C_2$-$C_7$-alkenyl or $C_2$-$C_7$-alkinyl.

6. A conjugate compound according to claim 1, whereby:

$R^{22a}$ and $R^{22b}$ represent methyl, ethyl, propyl, i-propyl, tert.butyl, CF₃, C₂F₅, F, Cl, nitro, CN, N₃, NH₂, CO₂-methyl, CO₂-ethyl, CO₂-propyl or CO₂-i-propyl.

7. Conjugate according to claim 1, whereby:

$R^{26}$ represents methyl, ethyl, propyl, i-propyl, t-butyl, CF₃, propenyl or butenyl.

8. A conjugate compound according to claim 1, whereby:

$R^{2a}$ represents hydrogen, and $R^{2b}$ represents methyl, ethyl, propyl, i-propyl, propenyl, butenyl, propinyl or butinyl; or $R^{2b}$ represents hydrogen, and $R^{2a}$ represents methyl, ethyl, propyl, i-propyl, propenyl, butenyl, propinyl or butinyl.

9. A conjugate compound according to claim 1, whereby the portion of the compound absent the linker-recognition unit of at least one of L¹, L² and L³, is selected from the group that consists of:

(4S,7R,8S,9S,13Z,16S(E))-4,8-Dihydroxy-5,5,7,9,13-pentamethyl-16-[1-methyl-2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-1-methyl-vinyl]-5,5,7,9,13-pentamethyl-oxacyclohexadec-13-ene-2,6-dione;

(4S,7R,8S,9S,13Z,16S(E))-16-[2-(2-Aminomethyl-thiazol-4-yl)-1-methyl-vinyl]-4,8-dihydroxy-5,5,7,9,13-pentamethyl-oxacyclohexadec-13-ene-2,6-dione;

(1S,3S(E),7S,10R,11S,12S,16R)-7,11-Dihydroxy-8,8,10,12,16-pentamethyl-3-[1-methyl-2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-1-methyl-vinyl]-8,8,10,12,16-pentamethyl-4,17-dioxa-bicyclo[14.1.0]-heptadecane-5,9-dione;

(1S,3S(E),7S,10R,11S,12S,16R)-3-[2-(2-Aminomethyl-thiazol-4-yl)-1-methyl-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(E))-4,8-Dihydroxy-7-ethyl-5,5,9,13-tetramethyl-16-[1-methyl-2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-1-methyl-vinyl]-7-ethyl-5,5,9,13-tetramethyl-oxacyclohexadec-13-ene-2,6-dione;

(4S,7R,8S,9S,13Z,16S(E))-16-[2-(2-Aminomethyl-thiazol-4-yl)-1-methyl-vinyl]-4,8-dihydroxy-7-ethyl-5,5,9,13-tetramethyl-oxacyclohexadec-13-ene-2,6-dione;

(1S,3S(E),7S,10R,11S,12S,16R)-7,11-Dihydroxy-10-ethyl-8,8,12,16-tetramethyl-3-[1-methyl-2-(2-methyl-thiazol-4-yl)-vinyl]-4,17-dioxa-bicyclo[14.1.0]-heptadecane-5,9-dione;

(1S,3S(E),7S,10R,11S,12S,16R)-7,11-Dihydroxy-3-[2-(2-hydroxymethyl-thiazol-4-yl)-1-methyl-vinyl]-10-ethyl-8,8,12,16-tetramethyl-4,17-dioxa-bicyclo[14.1.0]heptadecane-5,9-dione;

(1S,3S(E),7S,10R,11S,12S,16R)-3-[2-(2-Aminomethyl-thiazol-4-yl)-1-methyl-vinyl]-7,11-dihydroxy-10-ethyl-8,8,12,16-tetramethyl-4,17-dioxa-bicyclo[14.1.0]-heptadecane-5,9-dione;

(4S,7R,8S,9S,13Z,16S(Z))-4,8-Dihydroxy-5,5,7,9,13-pentamethyl-16-[1-fluoro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-fluoro-vinyl]-5,5,7,9,13-pentamethyl-oxacyclohexadec-13-ene-2,6-dione;

(4S,7R,8S,9S,13Z,16S(Z))-16-[2-(2-Aminomethyl-thiazol-4-yl)-1-fluoro-vinyl]-4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-fluoro-2-(2-methyl-thiazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-thiazol-4-yl)-1-fluoro-vinyl]-8,8,10,12,16-pentamethyl-4,17-dioxa-bicyclo[14.1.0]-heptadecane-5,9-dione;

(1S,3S(Z),7S,10R,11S,12S,16R)-3-[2-(2-Aminomethyl-thiazol-4-yl)-1-fluoro-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(Z))-4,8-Dihydroxy-5,5,7,9,13-pentamethyl-16-[1-chloro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-chloro-vinyl]-5,5,7,9,13-pentamethyl-oxacyclohexadec-13-ene-2,6-dione;

(4S,7R,8S,9S,13Z,16S(Z))-16-[2-(2-Aminomethyl-thiazol-4-yl)-1-chloro-vinyl]-4,8-dihydroxy-5,5,7,9,13-pentamethyl-oxacyclohexadec-13-ene-2,6-dione;

(1S,3S(Z),7S,10R,11S,12S,16R)-7,11-Dihydroxy-8,8,10,12,16-pentamethyl-3-[1-chloro-2-(2-methyl-thiazol-4-yl)-vinyl]-4,17-dioxa-bicyclo[14.1.0]heptadecane-5,9-dione;

(1S,3S(Z),7S,10R,11S,12S,16R)-7,11-Dihydroxy-3-[2-(2-hydroxymethyl-thiazol-4-yl)-1-chloro-vinyl]-8,8,10,12,16-pentamethyl-4,17-dioxa-bicyclo[14.1.0]-heptadecane-5,9-dione;

(1S,3S(Z),7S,10R,11S,12S,16R)-3-[2-(2-Aminomethyl-thiazol-4-yl)-1-cloro-vinyl]-7,11-dihydroxy-8,8,10,12,16-pentamethyl-4,17-dioxa-bicyclo[14.1.0]-heptadecane-5,9-dione;

(4S,7R,8S,9S,13Z,16S(Z))-4,8-Dihydroxy-7-ethyl-5,5,9,13-tetramethyl-16-[1-fluoro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-fluoro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-thiazol-4-yl)-1-fluoro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-fluoro-2-(2-methyl-thiazol-4-yl)-vinyl]-4,17-dioxa-bicyclo[14.1.0]-heptadecane-5,9-dione;

(1S,3S(Z),7S,10R,11S,12S,16R)-7,11-Dihydroxy-3-[2-(2-hydroxymethyl-thiazol-4-yl)-1-fluoro-vinyl]-10-ethyl-8,8,12,16-tetramethyl-4,17-dioxa-bicyclo[14.1.0]-heptadecane-5,9-dione;

(1S,3S(Z),7S,10R,11S,12S,16R)-3-[2-(2-Aminomethyl-thiazol-4-yl)-1-fluoro-vinyl]-7,11-dihydroxy-10-ethyl-8,8,12,16-tetramethyl-4,17-dioxa-bicyclo[14.1.0]-heptadecane-5,9-dione;

(4S,7R,8S,9S,13Z,16S(Z))-4,8-Dihydroxy-7-ethyl-5,5,9,13-tetramethyl-16-[1-chloro-2-(2-methyl-thiazol-4-yl)-vinyl]-oxacyclohexadec-13-ene-2,6-dione;

(4S,7R,8S,9S,13Z,16S(Z))-4,8-Dihydroxy-16-[2-(2-hydroxymethyl-thiazol-4-yl)-1-chloro-vinyl]-7-ethyl-5,5,9,13-tetramethyl-oxacyclohexadec-13-ene-2,6-dione;

(4S,7R,8S,9S,13Z,16S(Z))-16-[2-(2-Aminomethyl-thiazol-4-yl)-1-chloro-vinyl]-4,8-dihydroxy-7-ethyl-5,5,9,13-tetramethyl-oxacyclohexadec-13-ene-2,6-dione;

(1S,3S(Z),7S,10R,11S,12S,16R)-7,11-Dihydroxy-10-ethyl-8,8,12,16-tetramethyl-3-[1-chloro-2-(2-methyl-thiazol-4-yl)-vinyl]-4,17-dioxa-bicyclo[14.1.0]-heptadecane-5,9-dione;

(1S,3S(Z),7S,10R,11S,12S,16R)-7,11-Dihydroxy-3-[2-(2-hydroxymethyl-thiazol-4-yl)-1-chloro-vinyl]-10-ethyl-8,8,12,16-tetramethyl-4,17-dioxa-bicyclo[14.1.0]-heptadecane-5,9-dione;

(1S,3S(Z),7S,10R,11S,12S,16R)-3-[2-(2-Aminomethyl-thiazol-4-yl)-1-chloro-vinyl]-7,11-dihydroxy-10-ethyl-8,8,12,16-tetramethyl-4,17-dioxa-bicyclo[14.1.0]-heptadecane-5,9-dione;

(4S,7R,8S,9S,13Z,16S(E))-4,8-Dihydroxy-5,5,7,9,13-pentamethyl-16-[1-methyl-2-(2-pyridyl)-vinyl]-oxacyclohexadec-13-ene-2,6-dione;

(1S,3S(E),7S,10R,11S,12S,16R)-7,11-Dihydroxy-8,8,10,12,16-pentamethyl-3-[1-methyl-2-(2-pyridyl)-vinyl]-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[1-methyl-2-(2-pyridyl)-vinyl]-oxacyclohexadec-13-ene-2,6-dione;

(1S,3S(E),7S,10R,11S,12S,16R)-7,11-Dihydroxy-10-ethyl-8,8,12,16-tetramethyl-3-[1-methyl-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-fluoro-2-(2-pyridyl)-vinyl]-oxacyclohexadec-13-ene-2,6-dione;

(1S,3S(Z),7S,10R,11S,12S,16R)-7,11-Dihydroxy-8,8,10,12,16-pentamethyl-3-[1-fluoro-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-5,5,7,9,13-pentamethyl-16-[1-chloro-2-(2-pyridyl)-vinyl]-oxacyclohexadec-13-ene-2,6-dione;

(1S,3S(Z),7S,10R,11S,12S,16R)-7,11-Dihydroxy-8,8,10,12,16-pentamethyl-3-[1-chloro-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-7-ethyl-5,5,9,13-tetramethyl-16-[1-fluoro-2-(2-pyridyl)-vinyl]-oxacyclohexadec-13-ene-2,6-dione;

(1S,3S(Z),7S,10R,11S,12S,16R)-7,11-Dihydroxy-10-ethyl-8,8,12,16-tetramethyl-3-[1-fluoro-2-(2-pyridyl)-vinyl]-4,17-dioxa-bicyclo[14.1.0]heptadecane-5,9-dione;

(4S,7R,8S,9S,13Z,16S(Z))-4,8-Dihydroxy-7-ethyl-5,5,9,13-tetramethyl-16-[1-chloro-2-(2-pyridyl)-vinyl]-oxacyclohexadec-13-ene-2,6-dione;

(1S,3S(Z),7S,10R,11S,12S,16R)-7,11-Dihydroxy-10-ethyl-8,8,12,16-tetramethyl-3-[1-chloro-2-(2-pyridyl)-vinyl]-4,17-dioxa-bicyclo[14.1.0]heptadecane-5,9-dione;

(4S,7R,8S,9S,13Z,16S(E))-4,8-Dihydroxy-5,5,7,9,13-pentamethyl-16-[1-methyl-2-(2-methyl-oxazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-oxazol-4-yl)-1-methyl-vinyl]-5,5,7,9,13-pentamethyl-oxacyclohexadec-13-ene-2,6-dione;

(4S,7R,8S,9S,13Z,16S(E))-16-[2-(2-Aminomethyl-oxazol-4-yl)-1-methyl-vinyl]-4,8-dihydroxy-5,5,7,9,13-pentamethyl-oxacyclohexadec-13-ene-2,6-dione;

(1S,3S(E),7S,10R,11S,12S,16R)-7,11-Dihydroxy-8,8,10,
12,16-pentamethyl-3-[1-methyl-2-(2-methyl-oxazol-4-
yl)-vinyl]-4,17-dioxa-bicyclo[14.1.0]heptadecane-5,9-
dione;

(1S,3S(E),7S,10R,11S,12S,16R)-7,11-Dihydroxy-3-[2-
(2-hydroxymethyl-oxazol-4-yl)-1-methyl-vinyl]-8,8,
10,12,16-pentamethyl-4,17-dioxa-bicyclo[14.1.0]-hep-
tadecane-5,9-dione;

(1S,3S(E),7S,10R,11S,12S,16R)-3-[2-(2-Aminomethyl-
oxazol-4-yl)-1-methyl-vinyl]-7,11-dihydroxy-8,8,10,
12,16-pentamethyl-4,17-dioxa-bicyclo[14.1.0]-hepta-
decane-5,9-dione;

(4S,7R,8S,9S,13Z,16S(E))-4,8-Dihydroxy-7-ethyl-5,5,9,
13-tetramethyl-16-[1-methyl-2-(2-methyl-oxazol-4-
yl)-vinyl]-oxacyclohexadec-13-ene-2,6-dione;

(4S,7R,8S,9S,13Z,16S(E))-4,8-Dihydroxy-16-[2-(2-hy-
droxymethyl-oxazol-4-yl)-1-methyl-vinyl]-7-ethyl-5,
5,9,13-tetramethyl-oxacyclohexadec-13-ene-2,6-di-
one;

(4S,7R,8S,9S,13Z,16S(E))-16-[2-(2-Aminomethyl-ox-
azol-4-yl)-1-methyl-vinyl]-4,8-dihydroxy-7-ethyl-5,5,
9,13-tetramethyl-oxacyclohexadec-13-ene-2,6-dione;

(1S,3S(E),7S,10R,11S,12S,16R)-7,11-Dihydroxy-10-
ethyl-8,8,12,16-tetramethyl-3-[1-methyl-2-(2-methyl-
oxazol-4-yl)-vinyl]-4,17-dioxa-bicyclo[14.1.0]-hepta-
decane-5,9-dione;

(1S,3S(E),7S,10R,11S,12S,16R)-7,11-Dihydroxy-3-[2-
(2-hydroxymethyl-oxazol-4-yl)-1-methyl-vinyl]-10-
ethyl-8,8,12,16-tetramethyl-4,17-dioxa-bicyclo
[14.1.0]heptadecane-5,9-dione;

(1S,3S(E),7S,10R,11S,12S,16R)-3-[2-(2-Aminomethyl-
oxazol-4-yl)-1-methyl-vinyl]-7,11-dihydroxy-10-
ethyl-8,8,12,16-tetramethyl-4,17-dioxa-bicyclo
[14.1.0]-heptadecane-5,9-dione;

(4S,7R,8S,9S,13Z,16S(Z))-4,8-Dihydroxy-5,5,7,9,13-
pentamethyl-16-[1-fluoro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hy-
droxymethyl-oxazol-4-yl)-1-fluoro-vinyl]-5,5,7,9,13-
pentamethyl-oxacyclohexadec-13-ene-2,6-dione;

(4S,7R,8S,9S,13Z,16S(Z))-16-[2-(2-Aminomethyl-ox-
azol-4-yl)-1-fluoro-vinyl]-4,8-dihydroxy-5,5,7,9,13-
pentamethyl-oxacyclohexadec-13-ene-2,6-dione;

(1S,3S(Z),7S,10R,11S,12S,16R)-7,11-Dihydroxy-8,8,10,
12,16-pentamethyl-3-[1-fluoro-2-(2-methyl-oxazol-4-
yl)-vinyl]-4,17-dioxa-bicyclo[14.1.0]heptadecane-5,9-
dione;

(1S,3S(Z),7S,10R,11S,12S,16R)-7,11-Dihydroxy-3-[2-
(2-hydroxymethyl-oxazol-4-yl)-1-fluoro-vinyl]-8,8,10,
12,16-pentamethyl-4,17-dioxa-bicyclo[14.1.0]-hepta-
decane-5,9-dione;

(1S,3S(Z),7S,10R,11S,12S,16R)-3-[2-(2-Aminomethyl-
oxazol-4-yl)-1-fluoro-vinyl]-7,11-dihydroxy-8,8,10,
12,16-pentamethyl-4,17-dioxa-bicyclo[14.1.0]-hepta-
decane-5,9-dione;

(4S,7R,8S,9S,13Z,16S(Z))-4,8-Dihydroxy-5,5,7,9,13-
pentamethyl-16-[1-chloro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hy-
droxymethyl-oxazol-4-yl)-1-chloro-vinyl]-5,5,7,9,13-
pentamethyl-oxacyclohexadec-13-ene-2,6-dione;

(4S,7R,8S,9S,13Z,16S(Z))-16-[2-(2-Aminomethyl-ox-
azol-4-yl)-1-chloro-vinyl]-4,8-dihydroxy-5,5,7,9,13-
pentamethyl-oxacyclohexadec-13-ene-2,6-dione;

(1S,3S(Z),7S,10R,11S,12S,16R)-7,11-Dihydroxy-8,8,10,
12,16-pentamethyl-3-[1-chloro-2-(2-methyl-oxazol-4-
yl)-vinyl]-4,17-dioxa-bicyclo[14.1.0]heptadecane-5,9-
dione;

(1S,3S(Z),7S,10R,11S,12S,16R)-7,11-Dihydroxy-3-[2-
(2-hydroxymethyl-oxazol-4-yl)-1-chloro-vinyl]-8,8,
10,12,16-pentamethyl-4,17-dioxa-bicyclo[14.1.0]-hep-
tadecane-5,9-dione;

(1S,3S(Z),7S,10R,11S,12S,16R)-3-[2-(2-Aminomethyl-
oxazol-4-yl)-1-chloro-vinyl]-7,11-dihydroxy-8,8,10,
12,16-pentamethyl-4,17-dioxa-bicyclo[14.1.0]-hepta-
decane-5,9-dione;

(4S,7R,8S,9S,13Z,16S(Z))-4,8-Dihydroxy-7-ethyl-5,5,9,
13-tetramethyl-16-[1-fluoro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hy-
droxymethyl-oxazol-4-yl)-1-fluoro-vinyl]-7-ethyl-5,5,
9,13-tetramethyl-oxacyclohexadec-13-ene-2,6-dione;

(4S,7R,8S,9S,13Z,16S(Z))-16-[2-(2-Aminomethyl-ox-
azol-4-yl)-1-fluoro-vinyl]-4,8-dihydroxy-7-ethyl-5,5,
9,13-tetramethyl-oxacyclohexadec-13-ene-2,6-dione;

(1S,3S(Z),7S,10R,1S,12S,16R)-7,11-Dihydroxy-10-
ethyl-8,8,12,16-tetramethyl-3-[1-fluoro-2-(2-methyl-
oxazol-4-yl)-vinyl]-4,17-dioxa-bicyclo[14.1.0]-hepta-
decane-5,9-dione;

(1S,3S(Z),7S,10R,11S,12S,16R)-7,11-Dihydroxy-3-[2-
(2-hydroxymethyl-oxazol-4-yl)-1-fluoro-vinyl]-10-
ethyl-8,8,12,16-tetramethyl-4,17-dioxa-bicyclo
[14.1.0]heptadecane-5,9-dione;

(1S,3S(Z),7S,10R,10S,12S,16R)-3-[2-(2-Aminomethyl-
oxazol-4-yl)-1-fluoro-vinyl]-7,11-dihydroxy-10-ethyl-
8,8,12,16-tetramethyl-4,17-dioxa-bicyclo[14.1.0]-hep-
tadecane-5,9-dione;

(4S,7R,8S,9S,13Z,16S(Z))-4,8-Dihydroxy-7-ethyl-5,5,9,
13-tetramethyl-16-[1-chloro-2-(2-methyl-oxazol-4-yl)-
vinyl]-oxacyclohexadec-13-ene-2,6-dione;

(4S,7R,8S,9S,13Z,16S(Z))-4,8-Dihydroxy-16-[2-(2-hy-
droxymethyl-oxazol-4-yl)-1-chloro-vinyl]-7-ethyl-5,5,
9,13-tetramethyl-oxacyclohexadec-13-ene-2,6-dione;

(4S,7R,8S,9S,13Z,16S(Z))-16-[2-(2-Aminomethyl-ox-
azol-4-yl)-1-chloro-vinyl]-4,8-dihydroxy-7-ethyl-5,5,
9,13-tetramethyl-oxacyclohexadec-13-ene-2,6-dione;

(1S,3S(Z),7S,10R,11S,12S,16R)-7,11-Dihydroxy-10-
ethyl-8,8,12,16-tetramethyl-3-[1-chloro-2-(2-methyl-
oxazol-4-yl)-vinyl]-4,17-dioxa-bicyclo[14.1.0]-hepta-
decane-5,9-dione;

(1S,3S(Z),7S,10R,11S,12S,16R)-7,11-Dihydroxy-3-[2-
(2-hydroxymethyl-oxazol-4-yl)-1-chloro-vinyl]-10-
ethyl-8,8,12,16-tetramethyl-4,17-dioxa-bicyclo
[14.1.0]heptadecane-5,9-dione;

(1S,3S(Z),7S,10R,11S,12S,16R)-3-[2-(2-Aminomethyl-
oxazol-4-yl)-1-chloro-vinyl]-7,11-dihydroxy-10-ethyl-
8,8,12,16-tetramethyl-4,17-dioxa-bicyclo[14.1.0]-hep-
tadecane-5,9-dione;

(4S,7R,8S,9S,13Z,16S(E))-4,8-Dihydroxy-5,5,7,9,13-
pentamethyl-16-[2-(2-methyl-thiazol-4-yl)-vinyl]-ox-
acyclohexadec-13-ene-2,6-dione;

(4S,7R,8S,9S,13Z,16S(E))-4,8-Dihydroxy-16-[2-(2-hy-
droxymethyl-thiazol-4-yl)-vinyl]-5,5,7,9,13-pentam-
ethyl-oxacyclohexadec-13-ene-2,6-dione;

(4S,7R,8S,9S,13Z,16S(E))-16-[2-(2-Aminomethyl-thia-
zol-4-yl)-vinyl]-4,8-dihydroxy-5,5,7,9,13-pentam-
ethyl-oxacyclohexadec-13-ene-2,6-dione;

(1S,3S(E),7S,10R,11S,12S,16R)-7,11-Dihydroxy-8,8,10,
12,16-pentamethyl-3-[2-(2-methyl-thiazol-4-yl)-vi-
nyl]-4,17-dioxa-bicyclo[14.1.0]heptadecane-5,9-di-
one;

(1S,3S(E),7S,10R,11S,12S,16R)-7,11-Dihydroxy-3-[2-(2-hydroxymethyl-thiazol-4-yl)-vinyl]-8,8,10,12,16-pentamethyl-4,17-dioxa-bicyclo[14.1.0]heptadecane-5,9-dione;

(1S,3S(E),7S,10R,11S,12S,16R)-3-[2-(2-Aminomethyl-thiazol-4-yl)-vinyl]-7,11-dihydroxy-8,8,10,12,16-pentamethyl-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[2-(2-methyl-thiazol-4-yl)-vinyl]-oxacyclohexadec-13-ene-2,6-dione;

(4S,7R,8S,9S,13Z,16S(E))-4,8-Dihydroxy-16-[2-(2-hydroxymethyl-thiazol-4-yl)-vinyl]-7-ethyl-5,5,9,13-tetramethyl-oxacyclohexadec-13-ene-2,6-dione;

(4S,7R,8S,9S,13Z,16S(E))-16-[2-(2-Aminomethyl-thiazol-4-yl)-vinyl]-4,8-dihydroxy-7-ethyl-5,5,9,13-tetramethyl-oxacyclohexadec-13-ene-2,6-dione;

(1S,3S(E),7S,10R,11S,12S,16R)-7,11-Dihydroxy-10-ethyl-8,8,12,16-tetramethyl-3-[2-(2-methyl-thiazol-4-yl)-vinyl]-4,17-dioxa-bicyclo[14.1.0]heptadecane-5,9-dione;

(1S,3S(E),7S,10R,11S,12S,16R)-7,11-Dihydroxy-3-[2-(2-hydroxymethyl-thiazol-4-yl)-vinyl]-10-ethyl-8,8,12,16-tetramethyl-4,17-dioxa-bicyclo[14.1.0]-heptadecane-5,9-dione;

(1S,3S(E),7S,10R,11S,12S,16R)-3-[2-(2-Aminomethyl-thiazol-4-yl)-vinyl]-7,11-dihydroxy-10-ethyl-8,8,12,16-tetramethyl-4,17-dioxa-bicyclo[14.1.0]heptadecane-5,9-dione;

(4S,7R,8S,9S,13Z,16S(E))-4,8-Dihydroxy-5,5,7,9,13-pentamethyl-16-[2-(2-pyridyl)-vinyl]-oxacyclohexadec-13-ene-2,6-dione;

(1S,3S(E),7S,10R,11S,12S,16R)-7,11-Dihydroxy-8,8,10,12,16-pentamethyl-3-[2-(2-pyridyl)-vinyl]-4,17-dioxa-bicyclo[14.1.0]heptadecane-5,9-dione;

(4S,7R,8S,9S,13Z,16S(E))-4,8-Dihydroxy-7-ethyl-5,5,9,13-tetramethyl-16-[2-(2-pyridyl)-vinyl]-oxacyclohexadec-13-ene-2,6-dione;

(1S,3S(E),7S,10R,11S,12S,16R)-7,11-Dihydroxy-10-ethyl-8,8,12,16-tetramethyl-3-[2-(2-pyridyl)-vinyl]-4,17-dioxa-bicyclo[14.1.0]heptadecane-5,9-dione;

(4S,7R,8S,9S,13Z,16S)-4,8-Dihydroxy-5,5,7,9,13-pentamethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-5,5,7,9,13-pentamethyl-oxacyclohexadec-13-ene-2,6-dione;

(4S,7R,8S,9S,13Z,16S)-16-(2-Aminomethyl-benzothiazol-5-yl)-4,8-dihydroxy-5,5,7,9,13-pentamethyl-oxacyclohexadec-13-ene-2,6-dione;

(1S,3S,7S,10R,11S,12S,16R)-7,11-Dihydroxy-8,8,10,12,16-pentamethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-8,8,10,12,16-pentamethyl-4,17-dioxa-bicyclo[14.1.0]heptadecane-5,9-dione;

(1S,3S,7S,R,11S,12S,16R)-3-(2-Aminomethyl-benzothiazol-5-yl)-7,11-dihydroxy-8,8,10,12,16-pentamethyl-4,17-dioxa-bicyclo[14.1.0]heptadecane-5,9-dione;

(4S,7R,8S,9S,13Z,16S)-4,8-Dihydroxy-7-ethyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-ethyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-ethyl-5,5,9,13-tetramethyl-oxacyclohexadec-13-ene-2,6-dione;

(1S,3S,7S,10R,11S,12S,16R)-7,11-Dihydroxy-10-ethyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-ethyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-ethyl-8,8,12,16-tetramethyl-4,17-dioxa-bicyclo[14.1.0]heptadecane-5,9-dione;

(4S,7R,8S,9S,13Z,16S)-4,8-Dihydroxy-7-propyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-propyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-propyl-5,5,9,13-tetramethyl-oxacyclohexadec-13-ene-2,6-dione;

(1S,3S,7S,10R,11S,12S,16R)-7,11-Dihydroxy-10-propyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-propyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-propyl-8,8,12,16-tetramethyl-4,17-dioxa-bicyclo[14.1.0]heptadecane-5,9-dione;

(4S,7R,8S,9S,13Z,16S)-4,8-Dihydroxy-7-butyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-butyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-butyl-5,5,9,13-tetramethyl-oxacyclohexadec-13-ene-2,6-dione;

(1S,3S,7S,10R,11S,12S,16R)-7,11-Dihydroxy-10-butyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-butyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-butyl-8,8,12,16-tetramethyl-4,17-dioxa-bicyclo[14.1.0]heptadecane-5,9-dione;

(4S,7R,8S,9S,13Z,16S)-4,8-Dihydroxy-7-allyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-allyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-allyl-5,5,9,13-tetramethyl-oxacyclohexadec-13-ene-2,6-dione;

(1S,3S,7S,10R,11S,12S,16R)-7,11-Dihydroxy-10-allyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-allyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-allyl-8,8,12,16-tetramethyl-4,17-dioxa-bicyclo[14.1.0]heptadecane-5,9-dione;

(4S,7R,8S,9S,13Z,16S)-4,8-Dihydroxy-7-prop-2-inyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-prop-2-inyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-prop-2-inyl-5,5,9,13-tetramethyl-oxacyclohexadec-13-ene-2,6-dione;

(1S,3S,7S,10R,11S,12S,16R)-7,11-Dihydroxy-10-prop-2-inyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-prop-2-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzothiazol-5-yl)-7,11-dihydroxy-10-prop-2-inyl-8,8,12,16-tetramethyl-4,17-dioxa-bicyclo[14.1.0]-heptadecane-5,9-dione;

(4S,7R,8S,9S,13Z,16S)-4,8-Dihydroxy-7-but-3-enyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-but-3-enyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-but-3-enyl-5,5,9,13-tetramethyl-oxacyclohexadec-13-ene-2,6-dione;

(1S,3S,7S,10R,11S,12S,16R)-7,11-Dihydroxy-10-but-3-enyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-but-3-enyl-8,8,12,16-tetramethyl-4,17-dioxa-bicyclo[14.1.0]-heptadecane-5,9-dione;

(1S,3S,7S,10R,11S,12S,16R)-3-(2-Aminomethyl-benzothiazol-5-yl)-7,11-dihydroxy-10-but-3-enyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-inyl-5,5,9,13-tetramethyl-16-(2-methyl-benzothiazol-5-yl)-oxacyclohexadec-13-ene-2,6-dione;

(4S,7R,8S,9S,13Z,16S)-4,8-Dihydroxy-16-(2-hydroxymethyl-benzothiazol-5-yl)-7-but-3-inyl-5,5,9,13-tetramethyl-oxacyclohexadec-13-ene-2,6-dione;

(4S,7R,8S,9S,13Z,16S)-16-(2-Aminomethyl-benzothiazol-5-yl)-4,8-dihydroxy-7-but-3-inyl-5,5,9,13-tetramethyl-oxacyclohexadec-13-ene-2,6-dione;

(1S,3S,7S,10R,11S,12S,16R)-7,11-Dihydroxy-10-but-3-inyl-8,8,12,16-tetramethyl-3-(2-methyl-benzothiazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzothiazol-5-yl)-10-but-3-inyl-8,8,12,16-tetramethyl-4,17-dioxa-bicyclo[14.1.0]-heptadecane-5,9-dione;

(1S,3S,7S,10R,11S 12S,16R)-3-(2-Aminomethyl-benzothiazol-5-yl)-7,11-dihydroxy-10-but-3-inyl-8,8,12,16-tetramethyl-4,17-dioxa-bicyclo[14.1.0]heptadecane-5,9-dione;

(4S,7R,8S,9S,13Z,16S)-4,8-Dihydroxy-5,5,7,9,13-pentamethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-5,5,7,9,13-pentamethyl-oxacyclohexadec-13-ene-2,6-dione;

(4S,7R,8S,9S,13Z,16S)-16-(2-Aminomethyl-benzoxazol-5-yl)-4,8-dihydroxy-5,5,7,9,13-pentamethyl-oxacyclohexadec-13-ene-2,6-dione;

(1S,3S,7S,10R,11S,12S,16R)-7,11-Dihydroxy-8,8,10,12,16-pentamethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-8,8,10,12,16-pentamethyl-4,17-dioxa-bicyclo[14.1.0]heptadecane-5,9-dione;

(1S,3S,7S,R,11S,12S,16R)-3-(2-Aminomethyl-benzoxazol-5-yl)-7,11-dihydroxy-8,8,10,12,16-pentamethyl-4,17-dioxa-bicyclo[14.1.0]heptadecane-5,9-dione;

(4S,7R,8S,9S,13Z,16S)-4,8-Dihydroxy-7-ethyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-ethyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-ethyl-5,5,9,13-tetramethyl-oxacyclohexadec-13-ene-2,6-dione;

(1S,3S,7S,10R,11S,12S,16R)-7,11-Dihydroxy-10-ethyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-ethyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-ethyl-8,8,12,16-tetramethyl-4,17-dioxa-bicyclo[14.1.0]heptadecane-5,9-dione;

(4S,7R,8S,9S,13Z,16S)-4,8-Dihydroxy-7-propyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-propyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-propyl-5,5,9,13-tetramethyl-oxacyclohexadec-13-ene-2,6-dione;

(1S,3S,7S,10R,11S,12S,16R)-7,11-Dihydroxy-10-propyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-propyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-propyl-8,8,12,16-tetramethyl-4,17-dioxa-bicyclo[14.1.0]heptadecane-5,9-dione;

(4S,7R,8S,9S,13Z,16S)-4,8-Dihydroxy-7-butyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-butyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-butyl-5,5,9,13-tetramethyl-oxacyclohexadec-13-ene-2,6-dione;

(1S,3S,7S,10R,11S,12S,16R)-7,11-Dihydroxy-10-butyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-butyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-butyl-8,8,12,16-tetramethyl-4,17-dioxa-bicyclo[14.1.0]heptadecane-5,9-dione;

(4S,7R,8S,9S,13Z,16S)-4,8-Dihydroxy-7-allyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-allyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-allyl-5,5,9,13-tetramethyl-oxacyclohexadec-13-ene-2,6-dione;

(1S,3S,7S,10R,11S,12S,16R)-7,11-Dihydroxy-10-allyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-allyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-allyl-8,8,12,16-tetramethyl-4,17-dioxa-bicyclo[14.1.0]heptadecane-5,9-dione;

(4S,7R,8S,9S,13Z,16S)-4,8-Dihydroxy-7-prop-2-inyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-prop-2-inyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-prop-2-inyl-5,5,9,13-tetramethyl-oxacyclohexadec-13-ene-2,6-dione;

(1S,3S,7S,10R,11S,12S,16R)-7,11-Dihydroxy-10-prop-2-inyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-prop-2-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-prop-2-inyl-8,8,12,16-tetramethyl-4,17-dioxa-bicyclo[14.1.0]-heptadecane-5,9-dione;

(4S,7R,8S,9S,13Z,16S)-4,8-Dihydroxy-7-but-3-enyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-but-3-enyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-but-3-enyl-5,5,9,13-tetramethyl-oxacyclohexadec-13-ene-2,6-dione;

(1S,3S,7S,10R,11S,12S,16R)-7,11-Dihydroxy-10-but-3-enyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-but-3-enyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-but-3-enyl-8,8,12,16-tetramethyl-4,17-dioxa-bicyclo[14.1.0]heptadecane-5,9-dione;

(4S,7R,8S,9S,13Z,16S)-4,8-Dihydroxy-7-but-3-inyl-5,5,9,13-tetramethyl-16-(2-methyl-benzoxazol-5-yl)-oxacyclohexadec-13-ene-2,6-dione;

(4S,7R,8S,9S,13Z,16S)-4,8-Dihydroxy-16-(2-hydroxymethyl-benzoxazol-5-yl)-7-but-3-inyl-5,5,9,13-tetramethyl-oxacyclohexadec-13-ene-2,6-dione;

(4S,7R,8S,9S,13Z,16S)-16-(2-Aminomethyl-benzoxazol-5-yl)-4,8-dihydroxy-7-but-3-inyl-5,5,9,13-tetramethyl-oxacyclohexadec-13-ene-2,6-dione;

(1S,3S,7S,10R,11S,12S,16R)-7,11-Dihydroxy-10-but-3-inyl-8,8,12,16-tetramethyl-3-(2-methyl-benzoxazol-5-yl)-4,17-dioxa-bicyclo[14.1.0]heptadecane-5,9-dione;

(1S,3S,7S,10R,11S,12S,16R)-7,11-Dihydroxy-3-(2-hydroxymethyl-benzoxazol-5-yl)-10-but-3-inyl-8,8,12,16-tetramethyl-4,17-dioxa-bicyclo[14.1.0]heptadecane-5,9-dione;

(1S,3S,7S,10R,11S,12S,16R)-3-(2-Aminomethyl-benzoxazol-5-yl)-7,11-dihydroxy-10-but-3-inyl-8,8,12,16-tetramethyl-4,17-dioxa-bicyclo[14.1.0]heptadecane-5,9-dione;

whereby the hydrogen atoms are replaced by radicals $L^1$-$L^3$ in the positions indicated in formula (I).

10. A conjugate compound according claim 1, whereby the conjugate contains more than one EGrecognition unit, and whereby the recognition units are identical.

11. A process for the production of a conjugate compound according to claim 1, which comprises reacting:

a compound of formula (I), in which the substituents have the meanings that are mentioned in claim 1, but the condition that at least one substituent $L^1$, $L^2$, or $L^4$ represents a linker-recognition unit of formula (III) need not be met, and at least one substituent $L^1 L^2$, or $L^4$ represents hydrogen, a group (=O)Cl or a group C(=S)Cl, with a linker-recognition unit, which is selected from the group that consists of: a linker-recognition unit of formula (III$^1$)

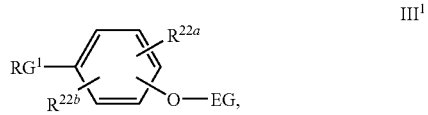

in which

RG$^1$ represents an O=C=N group or an S=C=N group or an O=C=N—CH$_2$ group or an S=C=N—CH$_2$ group; and $R^{22a}$, $R^{22b}$ and EG have the meanings that are mentioned in claim 1; or a linker-recognition unit of formula (III$^2$):

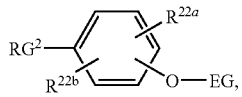

in which RG$^2$ represents an HO—CH$^2$ group or an HNR$^{23}$—CH$_2$ group; and $R^{22a}$, $R^{22b}$ and EG have the meanings that are mentioned in claim 1; but with the condition that the following compounds are not included:

- (4-Hydroxymethyl)phenyl-2,3,4,6-tetra-O-acetyl-α-D-galactopyranoside;
- (2-Hydroxymethyl)phenyl-2,3,4,6-tetra-O-acetyl-α-D-galactopyranoside;
- (4-Hydroxymethyl)phenyl-2,3,4-tri-O-acetyl-β-D-glucuronide-6-methyl ester;
- (2-Hydroxymethyl)phenyl-2,3,4-tri-O-acetyl-β-D-glucuronide-6-methyl ester;
- (4-Hydroxymethyl)phenyl-2,3,4,6-tetra-O-acetyl-β-D-glucopyranoside;
- (2-Hydroxymethyl-4-nitro)phenyl-2,3,4,6-tetra-O-acetyl-α-D-galactopyranoside;
- (4-Hydroxymethyl-2-nitro)phenyl-2,3,4,6-tetra-O-acetyl-α-D-galactopyranoside;
- (2-Hydroxymethyl-4-nitro)phenyl-2,3,4-tri-O-acetyl-β-D-glucuronide 6-methyl ester;
- (4-Hydroxymethyl-2-nitro)phenyl-2,3,4-tri-O-acetyl-β-D-glucuronide-6-methyl ester;
- (2-Chloro-4-hydroxymethyl)phenyl-2,3,4,6-tetra-O-acetyl-α-D-galactopyranoside; and
- (2-Chloro-4-hydroxymethyl)phenyl-2,3,4-tri-O-acetyl-β-D-glucuronide-6-methyl ester;

or a linker-recognition unit of general formula (III$^3$):

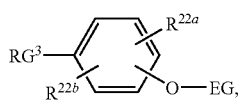

in which

RG$^3$ represents a Hal-C(=O)—CH$_2$ group or a Hal-C(=S)—CH$_2$ group or an $R^{27}$—C(=O)—O—C(=O)—CH$_2$ group or an $R^{27}$—C(=O)—O—C(=S)—CH$_2$ group or a

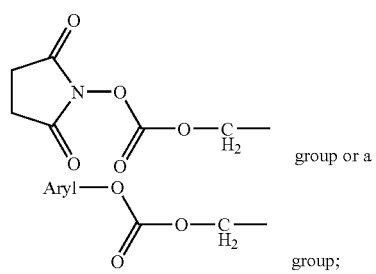

group or a group;

$R^{27}$ is $C_1$-$C_{10}$ alkyl, aryl or aralkyl; and $R^{22a}$, $R^{22b}$ and EG have the meanings that are mentioned in claim 1; but with the condition that the following compounds are not included:

- 2,5-Dioxopyrrolidin-1-yl-[4-(2,3,4,6-tetra-O-acetyl-α-D-galactopyranosyl)-benzyl]carbonate;
- 2,5-Dioxopyrrolidin-1-yl-[2-(2,3,4,6-tetra-O-acetyl-α-D-galactopyranosyl)-benzyl]carbonate;
- 2,5-Dioxopyrrolidin-1-yl-[4-((2,3,4-tri-O-acetyl-β-D-glucopyranosyl)-methyluronate)benzyl]carbonate;
- 4-Nitrophenyl-[2-((2,3,4-tri-O-acetyl-β-D-glucopyranosyl)methyluronate)-benzyl]carbonate;
- 2,5-Dioxopyrrolidin-1-yl-[4-(2,3,4,6-tetra-O-acetyl-β-D-glucopyranosyl)-benzyl]carbonate;
- 4-Nitrophenyl-[2-(2,3,4,6-tetra-O-acetyl-α-D-galactopyranosyl)-5-nitrobenzyl]carbonate;
- 4-Nitrophenyl-[2-((2,3,4-tri-O-acetyl-β-D-glucopyranosyl)methyluronate)-5-nitrobenzyl]carbonate;
- 4-Nitrophenyl-[4-methoxy-5-nitro-2-((2,3,4-tri-O-acetyl-β-D-glucopyranosyl)methyluronate)benzyl]carbonate;
- 4-Nitrophenyl-[4-((2,3,4-tri-O-acetyl-β-D-glucopyranosyl)methyluronate)-5-nitrobenzyl]carbonate;
- 4-Chlorophenyl-[2-((2,3,4-tri-O-acetyl-β-D-glucopyranosyl)methyluronate)-5-nitrobenzyl]carbonate.

12. A pharmaceutical or medication composition which comprises a conjugate compound according to claim 1 and a pharmaceutically acceptable carrier.

13. A method for treating a primary tumor and/or metastases that are not operatively accessible in a patient which comprises administering to the patient an effective amount of a conjugate compound of claim 1.

14. A method according to claim 13 whereby the conjugate compound is administered in combination with one or more other substances to trigger enhanced cell death (apoptosis) and necrosis.

15. A method according to claim 13 whereby the conjugate compound is administered in combination with one or more L19 constructs.

16. A conjugate compound according to claim 1, wherein, in each instance, aryl is selected from the group consisting of phenyl, naphthyi, furyl, thienyl, pyridyl, pyrazolyl, pyrimidinyl, oxazolyl, pyridazinyl, pyrazinyl, quinolyl, thiazolyl, benzothiazolyl, benzoxazolyl, which are optionally substituted in one or more places by halogen, OH, O-alkyl, CO$_2$H, CO$_2$-alkyl, —NH$_2$, —NO$_2$, —N$_3$, —CN, $C_1$-$C_{20}$-alkyl, $C_1$-$C_{20}$-acyl, or $C_1$-$C_{20}$-acyloxy groups.

17. A conjugate compound according to claim 1, wherein the bi- or tricyclic aromatic or heteroaromatic radical for W is selected from the group consisting of naphthyl, anthryl, benzothiazolyl, benzoxazolyl, benzimidazolyi, quinolyl, isoquinolyl, benzoxazinyl, benzofuranyl, indolyl, indazolyl, quinoxalinyl, tetrahydroisoquinolinyl, tetrahydroquinolinyl, thienopyridinyl, pyridopyridinyl, benzopyrazolyl, benzotriazolyl, or dihydroindolyl, which are optionally substituted in one or more places by halogen, OH, O-alkyl, CO$_2$H, CO$_2$-alkyl, —NH$_2$, —NO$_2$, —N$_3$, —CN, $C_1$-$C_{20}$-alkyl, $C_1$-$C_{20}$-acyl, or $C_1$-$C_{20}$-acyloxy groups.

18. A conjugate compound according to claim 1, wherein the aralkyl groups, in each case, are selected from the group consisting of benzyl, phenylethyl, naphthylmethyl, naphthylethyl, flirylmethyl, thienylethyl, and pyridyipropyl, which are optionally substituted in one or more places by halogen, OH, O-alkyl, CO$_2$H, CO$_2$-alkyl, —NO$_2$, —N$_3$, —CN, $C_1$-$C_{20}$-alkyl, $C_1$-$C_{20}$-acyl, or $C_1$-$C_{20}$-acyloxy groups.

19. A conjugate compound according to claim 1, wherein the protective groups PG are each selected from: tris($C_1$-$C_{20}$ alkyl)silyl, bis($C_1$-$C_{20}$ alkyl)-arylsilyl, ($C_1$-$C_{20}$ alkyl)-diarylsilyl, tris(aralkyl)-silyl, $C_1$-$C_{20}$-alkyl, $C_2$-$C_{20}$-alkenyl, $C_4$-$C_7$-cycloalkyl which optionally contains an oxygen atom in the ring, aryl, $C_7$-$C_{20}$-aralkyl, $C_1$-$C_{20}$-acyl, aroyl, $C_1$-$C_{20}$-alkoxycarbonyl, $C_1$-$C_{20}$-alkylsulfonyl, arylsulfonyl or the amino protective groups Alloc, Boc, Z, benzyl, f-Moc, Troc, Stabase or beuzostabase.

20. A conjugate compound of claim 1, wherein m is 3 to 5.

21. A method according to claim 15 whereby the conjugate compound is administered in combination with EDB-fibronectin or a combrestatin A4 prodrug.

* * * * *

UNITED STATES PATENT AND TRADEMARK OFFICE
CERTIFICATE OF CORRECTION

PATENT NO.      : 7,605,136 B2                                            Page 1 of 1
APPLICATION NO. : 10/728098
DATED           : October 20, 2009
INVENTOR(S)     : Bosslet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 477 days.

Signed and Sealed this

Fourteenth Day of December, 2010

David J. Kappos
*Director of the United States Patent and Trademark Office*